US012716070B2

(12) United States Patent
Tang

(10) Patent No.: US 12,716,070 B2
(45) Date of Patent: Aug. 25, 2026

(54) DISPERSINS EXPRESSED WITH AMYLASE SIGNAL PEPTIDES

(71) Applicant: Novozymes A/S, Bagsvaerd (DK)

(72) Inventor: Maria Tang, Fairfield, CA (US)

(73) Assignee: Novozymes A/S, Bagsvaerd (DK)

( * ) Notice: Subject to any disclaimer, the term of this patent is extended or adjusted under 35 U.S.C. 154(b) by 525 days.

(21) Appl. No.: 18/042,168

(22) PCT Filed: Jul. 2, 2021

(86) PCT No.: PCT/EP2021/068361

§ 371 (c)(1),
(2) Date: Feb. 17, 2023

(87) PCT Pub. No.: WO2022/037836

PCT Pub. Date: Feb. 24, 2022

(65) Prior Publication Data

US 2023/0313209 A1 Oct. 5, 2023

Related U.S. Application Data

(60) Provisional application No. 63/067,032, filed on Aug. 18, 2020.

(51) Int. Cl.
*C12N 15/75* (2006.01)
*C12N 9/24* (2006.01)
*C12N 9/28* (2006.01)

(52) U.S. Cl.
CPC ........... *C12N 15/75* (2013.01); *C12N 9/2402* (2013.01); *C12N 9/2417* (2013.01); *C12Y 302/01001* (2013.01); *C12Y 302/01052* (2013.01)

(58) Field of Classification Search
CPC .... C12N 15/75; C12N 9/2402; C12N 9/2417; C12Y 302/01001; C12Y 302/01052; C07K 2319/02; C12R 2001/10
See application file for complete search history.

(56) References Cited

U.S. PATENT DOCUMENTS 5,364,782 A * 11/1994 Quax .................. C12N 9/2414 435/320.1
6,228,614 B1 * 5/2001 Conneely .............. C07K 14/79 435/320.1
9,206,434 B2 * 12/2015 Hau ........................ C12P 7/065
9,909,115 B2 * 3/2018 Borchert .................. C12N 9/88
10,626,354 B2 * 4/2020 Ooehlenschlaeger ....................... C12Y 302/01052
10,954,478 B2 * 3/2021 Oehlenschlaeger . C11D 3/3953

FOREIGN PATENT DOCUMENTS

WO 1998050512 A1 11/1998
WO 2004061117 A2 7/2004
WO 2010151787 A1 12/2010
WO 2012025577 A1 3/2012
WO 2014206806 A1 12/2014
WO 2017186936 A1 11/2017
WO 2017186937 A1 11/2017
WO 2017186943 A1 11/2017
WO 2019055261 A1 3/2019
WO 2019086526 A1 5/2019

OTHER PUBLICATIONS

Broun et al., Catalytic plasticity of fatty acid modification enzymes underlying chemical diversity of plant lipids. Science, 1998, vol. 282: 1315-1317. (Year: 1998).*
Devos et al., Practical limits of function prediction. Proteins: Structure, Function, and Genetics. 2000, vol. 41: 98-107. (Year: 2000).*
Seffernick et al., Melamine deaminase and Atrazine chlorohydrolase: 98 percent identical but functionally different. J. Bacteriol., 2001, vol. 183 (8): 2405-2410. (Year: 2001).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Chica et al., Semi-rational approaches to engineering enzyme activity: combining the benefits of directed evolution and rational design. Curr. Opi. Biotechnol., 2005, vol. 16: 378-384. (Year: 2005).*
Guller-Gane et al., Overcoming the Refractory Expression of Secreted Recombinant Proteins in Mammalian Cells through Modification of the Signal Peptide and Adjacent Amino Acids. PLOS ONE, 2016, DOI:10.1371/journal.pone.0155340, pp. 1-15. (Year: 2016).*
Guo et al., Protein tolerance to random amino acid change. PNAS., 2004, vol. 101 (25): 9205-9210. (Year: 2004).*
Sen et al., Developments in directed evolution for improving enzyme functions. Appl. Biochem. Biotechnol., 2007, vol. 143: 212-223. (Year: 2007).*
Yamabhai et al., 2008, Journal of Biotechnology, 133, 50-57.
Yamaguchi et al., 1993, Bioscience, Biotechnology and Biochemistry, 57(8), 1384-1386.
Armenteros et al., Nature Biotechnol, 2019, 420-423, 37.
Caspers et al., Applied Microbiology and Biotechnology, 2010, 1877-1885, 86(6).
Contreras et al., PLASMID, 2010, 170-176, 64(3).

* cited by examiner

*Primary Examiner* — Ganapathirama Raghu
(74) *Attorney, Agent, or Firm* — Eric J. Fechter

(57) ABSTRACT

The present invention relates to nucleic acid constructs comprising a first polynucleotide encoding a signal peptide from a bacterial alpha-amylase a second polynucleotide encoding a polypeptide having hexosaminidase activity; expression vectors and host cells comprising said nucleic acid constructs; and methods for producing polypeptides having hexosaminidase activity.

18 Claims, 4 Drawing Sheets

Specification includes a Sequence Listing.

DISPERSINS EXPRESSED WITH AMYLASE SIGNAL PEPTIDES

CROSS-REFERENCE TO RELATED APPLICATIONS

This application is a 35 U.S.C. 371 national application of PCT/EP2021/068361, filed Jul. 2, 2021, which claims priority or the benefit from U.S. Provisional Application Ser. No. 63/067,032, filed Aug. 18, 2020. The contents of these applications are fully incorporated herein by reference.

REFERENCE TO A SEQUENCE LISTING

This application contains a Sequence Listing in computer readable form. The contents of the electronic sequence listing created on July 2. 2021, named 15066-WO-PCT seg.list.txt and 35 KB in size, is hereby incorporated by reference in its entirety.

FIELD OF THE INVENTION

The present invention relates to nucleic acid constructs comprising a first polynucleotide en-coding a signal peptide from a bacterial alpha-amylase a second polynucleotide encoding a polypep-tide having hexosaminidase activity; expression vectors and host cells comprising said nucleic acid constructs; and methods for producing polypeptides having hexosaminidase activity.

BACKGROUND OF THE INVENTION

Product development in industrial biotechnology includes a continuous challenge to increase enzyme yields at large scale to reduce costs. Two major approaches have been used for this purpose in the last decades. The first one is based on classical mutagenesis and screening. Here, the specific genetic modification is not predefined, and the main requirement is a screening assay that is sensitive to detect increments in yield. High-throughput screening enables large numbers of mutants to be screened in search for the desired phenotype, i.e., higher enzyme yields. The second approach includes numerous strategies ranging from the use of stronger promoters and multi-copy strains to ensure high expression of the gene of interest to the use of codon-optimized gene sequences to aid translation. However, high-level production of a given protein may in turn trigger several bottlenecks in the cellular machinery for secretion of the enzyme of interest into the medium, emphasizing the need for further optimization strategies.

Signal peptides (SPs) are short amino acid sequences present in the amino terminus of many newly synthesized polypeptides that target these into or across cellular membranes, thereby aiding maturation and secretion. The amino acid sequence of the SP influences secretion efficiency and thereby the yield of the polypeptide manufacturing process. Bioinformatic tools such as SignalP and SignalP5 can predict SPs from amino acid sequences, but most cannot distinguish between various types of SPs (Armenteros et al., *Nat. Biotechnol.* 37: 420-423, 2019). Moreover, a large degree of redundancy in the amino acid sequence of SPs makes it difficult to predict the efficiency of any given SP for production of enzymes at industrial scale. Hence, SP selection is an important step for manufacturing of recombinant proteins, but the optimal combination of signal peptide and mature protein is very context dependent and not easy to predict.

Dispersins are a subgroup of the glycoside hydrolase 20 (GH20) family that catalyse the hydrolysis of β-1,6-glycosidic linkages of N-acetyl-glucosamine polymers (poly-N-acetylglucosamine, PNAG), which are found in, e.g. biofilm produced by bacteria. In many cases, biofilm formation is unwanted, and biofilm removal is desired in many applications, including medical cleaning, laundry, dishwashing, wound care, and oral care. For instance, WO 2004/061117 A2 (Kane Biotech) describes use of compositions comprising Dispersin B (DspB) for reducing and preventing biofilm caused by poly-N-acetylglucosamine-producing bacteria, WO 1998/50512 (Procter and Gamble) provides laundry or cleaning products comprising one or more hexosaminidase enzymes, and WO 2017/186943 (Novozymes A/S) discloses dispersins suitable for use in detergents and for deep cleaning of items such as laundry and cleaning process.

SUMMARY OF THE INVENTION

The present invention is based on the surprising and inventive finding that expression of dispersins with a signal peptide from a bacterial alpha-amylase provides an improved yield of the dispersins compared to expression of the same dispersins with their native or other signal peptides.

In a first aspect, the present invention relates to nucleic acid constructs comprising:

a) first polynucleotide encoding a signal peptide from a bacterial alpha-amylase; and b) a second polynucleotide encoding a polypeptide having hexosaminidase activity;

wherein the first polynucleotide and the second polynucleotide are operably linked in translational fusion.

In a second aspect, the present invention relates to expression vectors comprising nucleic acid constructs of the first aspect.

In a third aspect, the present invention relates to bacterial host cells comprising nucleic acid constructs of the first aspect and/or expression vectors of the second aspect.

In a fourth aspect, the present invention relates to methods for producing polypeptides having hexosaminidase activity.

SEQUENCE OVERVIEW

Figure 1:
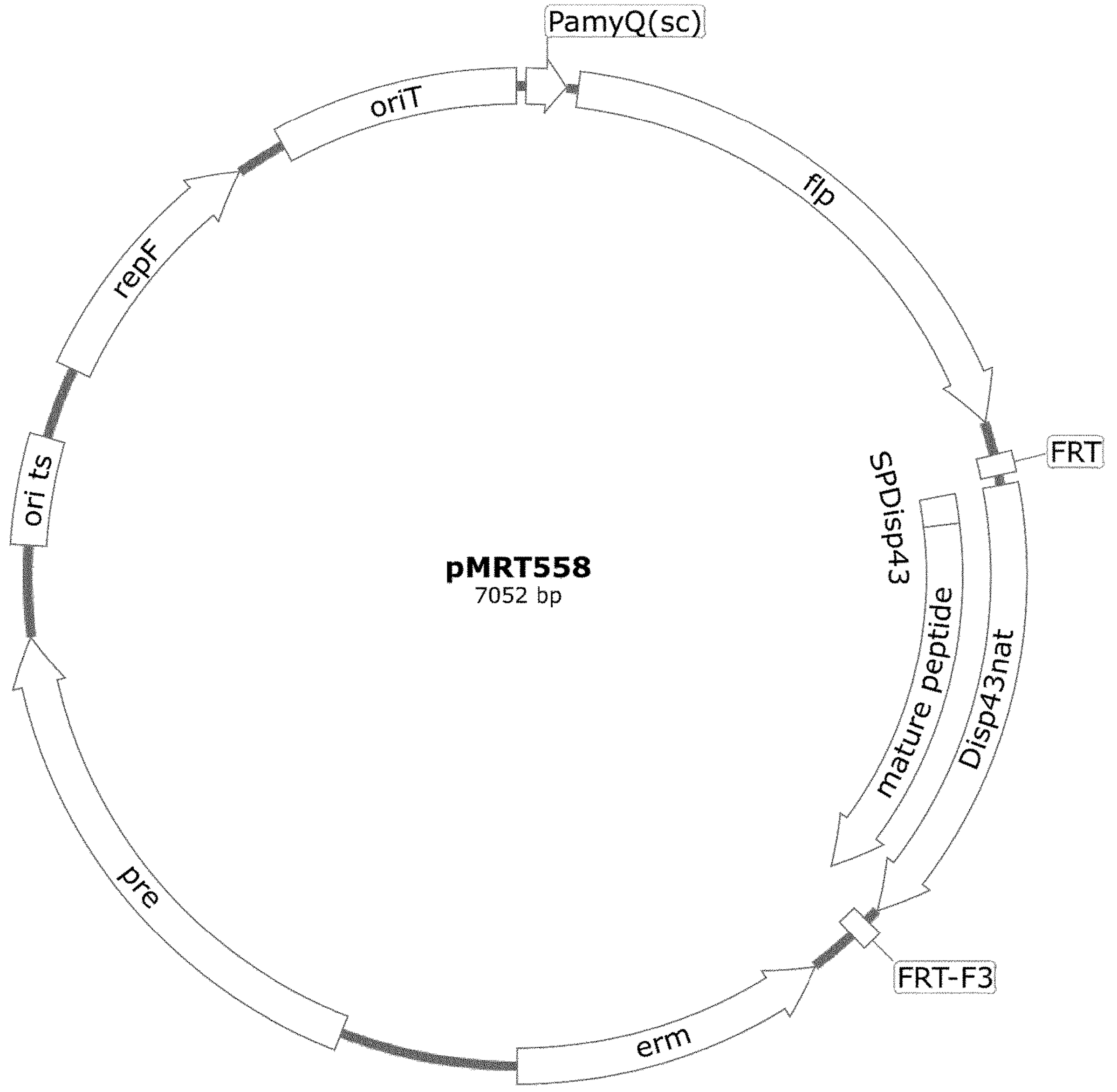
FIG. 1 shows a plasmid map of pMRT558.

SEQ ID NO: 1 is the AmyL signal peptide coding sequence.

SEQ ID NO: 2 is AmyL signal peptide.

SEQ ID NO: 3 is the Disp43nat coding sequence.

SEQ ID NO: 4 is Disp43nat.

SEQ ID NO: 5 is the SPamyLDisp43syn coding sequence.

SEQ ID NO: 6 is SPamyLDisp43syn.

SEQ ID NO: 7 is the SPaprHDisp45 coding sequence.

SEQ ID NO: 8 is SPaprHDisp45.

SEQ ID NO: 9 is the SPamyLDisp45syn coding sequence.

SEQ ID NO: 10 is SPamyLDisp45syn.

SEQ ID NO: 11 is the [VIM][LIV]G[GAV]DE[VI][PSA] motif.

Definitions cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Clade: The term "clade" means a group of polypeptides clustered together based on homologous features traced to a common ancestor. Polypeptide clades can be visualized as phylogenetic trees and a clade is a group of polypeptides that consists of a common ancestor and all its lineal descendants. Polypeptides forming a group within the clade (a subclade) of the phylogenetic tree can also share common properties and are more closely related than other polypeptides in the clade.

Coding sequence: The term "coding sequence" means a polynucleotide, which directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a variant of the present invention. Each control sequence may be native (i.e., from the same gene) or foreign (i.e., from a different gene) to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

Dispersin: The term "dispersin" and the abbreviations "Dsp" or "Disp" means a polypeptide having hexosaminidase activity (EC 3.2.1.-) that catalyzes the hydrolysis of β-1,6-glycosidic linkages of N-acetyl-glucosamine polymers (poly-N-acetylglucosamine, PNAG) found, e.g. in biofilm, EPS, cell debris and other biosoils. Thus, dispersins are enzymes having beta-1,6-N-acetylglucosaminidase activity or poly-beta-1,6-N-actylglucosamin (PNAG) activity. For purposes of the present invention, dispersin activity, i.e., beta-1,6-N-acetylglucosaminidase activity may be determined according to the procedures described in the "Materials and Methods" section of the Examples. The terms "dispersin", "Dsp", "Disp", and "polypeptide having hexosaminidase acitivity" are used interchangeably herein.

Expression: The term "expression" includes any step involved in the production of a variant including, but not limited to, transcription, post-transcriptional modification, translation, post-translational modification, and secretion.

Expression vector: The term "expression vector" means a linear or circular DNA molecule that comprises a polynucleotide encoding a variant and is operably linked to control sequences that provide for its expression.

Fragment: The term "fragment" means a polypeptide having one or more (e.g. several) amino acids absent from the amino and/or carboxyl terminus of a mature polypeptide; wherein the fragment has hexosaminidase activity.

Heterologous: With respect to a host cell, the term "heterologous" means that a polypeptide or nucleic acid does not naturally occur in the host cell. With respect to a polypeptide or nucleic acid, the term "heterologous" means that a control sequence, e.g. a promoter, or a domain of a polypeptide or polynucleotide is not naturally associated with the polypeptide or polynucleotide. Thus, a heterologous promoter is a promoter that is not naturally associated with the polynucleotide to which it is operably linked.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a polypeptide, nucleic acid, cell, or other specified material or component that is separated from at least one other material or component with which it is naturally associated as found in nature, including but not limited to, for example, other proteins, nucleic acids, cells, etc. An isolated polypeptide includes, but is not limited to, a culture or broth containing the secreted polypeptide.

Mature polypeptide: The term "mature polypeptide" means a polypeptide in its mature form following translation and any post-translational modifications such as N-terminal processing (e.g. removal of signal peptide), C-terminal truncation, glycosylation, phosphorylation, etc. It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g. having a different C-terminal and/or N-terminal amino acid) as compared to another host cell expressing the same polynucleotide. In some aspects, the mature polypeptide is amino acids 1 to 324 of SEQ ID NO: 4 and amino acids −25 to −1 of SEQ ID NO: 4 are a signal peptide. In some aspects, the mature polypeptide is amino acids 1 to 325 of SEQ ID NO: 6 and amino acids −28 to −1 of SEQ ID NO: 6 are a signal peptide. In some aspects, the mature polypeptide is amino acids 1 to 324 of SEQ ID NO: 8 and amino acids −27 to −1 of SEQ ID NO: 8 are a signal peptide. In some aspects, the mature polypeptide is amino acids 1 to 325 of SEQ ID NO: 10 and amino acids −28 to −1 of SEQ ID NO: 10 are a signal peptide.

Mature polypeptide coding sequence: The term "mature polypeptide coding sequence" means a polynucleotide that encodes a mature polypeptide having hexosaminidase activity. In some aspects, the mature polypeptide coding sequence is nucleotides 76 to 1047 of SEQ ID NO: 3 and nucleotides 1 to 75 of SEQ ID NO: 3 encode a signal peptide. In some aspects, the mature polypeptide coding sequence is nucleotides 85 to 1059 of SEQ ID NO: 5 and nucleotides 1 to 84 of SEQ ID NO: 5 encode a signal peptide. In some aspects, the mature polypeptide coding sequence is nucleotides 82 to 1053 of SEQ ID NO: 7 and nucleotides 1 to 81 of SEQ ID NO: 7 encode a signal peptide. In some aspects, the mature polypeptide coding sequence is nucleotides 85 to 1059 of SEQ ID NO: 9 and nucleotides 1 to 84 of SEQ ID NO: 9 encode a signal peptide.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Parent: The term "parent" means a polypeptide having hexosaminidase activity to which an alteration is made to produce variants of the present invention. The parent may be a naturally occurring (wild-type) polypeptide or a variant or fragment thereof.

Recombinant: The term "recombinant," when used in reference to a cell, nucleic acid, protein or vector, means that it has been modified from its native state. Thus, for example, recombinant cells express genes that are not found within the native (non-recombinant) form of the cell, or express native genes at different levels or under different conditions than found in nature. Recombinant nucleic acids differ from a native sequence by one or more nucleotides and/or are operably linked to heterologous sequences, e.g. a heterologous promoter in an expression vector. Recombinant proteins may differ from a native sequence by one or more amino acids and/or are fused with heterologous sequences. A vector comprising a nucleic acid encoding a polypeptide is a recombinant vector. The term "recombinant" is synonymous with "genetically modified" and "transgenic".

Sequence identity: The relatedness between two amino acid sequences or between two nucleotide sequences is described by the parameter "sequence identity".

For purposes of the present invention, the sequence identity between two amino acid sequences is determined as the output of "longest identity" using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 6.6.0 or later. The parameters used are a gap open penalty of 10, a gap extension penalty of 0.5, and the EBLOSUM62 (EMBOSS version of BLOSUM62) substitution matrix. In order for the Needle program to report the longest identity, the -nobrief option must be specified in the command line. The output of Needle labeled "longest identity" is calculated as follows:

(Identical Residues ×100)/(Length of Alignment−Total Number of Gaps in Alignment)

For purposes of the present invention, the sequence identity between two polynucleotide sequences is determined as the output of "longest identity" using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 6.6.0 or later. The parameters used are a gap open penalty of 10, a gap extension penalty of 0.5, and the EDNAFULL (EMBOSS version of NCBI NUC4.4) substitution matrix. In order for the Needle program to report the longest identity, the nobrief option must be specified in the command line. The output of Needle labeled "longest identity" is calculated as follows:

(Identical Deoxyribonucleotides×100)/(Length of Alignment−Total Number of Gaps in Alignment) (Identical Deoxyribonucleotides×100)/(Length of the Alignment)

Variant: The term "variant" means a polypeptide having hexosaminidase activity, comprising a substitution, an insertion, and/or a deletion, at one or more (e.g. several) positions compared to the parent. A substitution means replacement of the amino acid occupying a position with a different amino acid; a deletion means removal of the amino acid occupying a position; and an insertion means adding an amino acid adjacent to and immediately following the amino acid occupying a position.

Motif Nomenclature

For purposes of the present invention, the nomenclature [IV] or [I/V] means that the amino acid at this position may be isoleucine (Ile, I) or valine (Val, V). Likewise, the nomenclature [LVI] and [L/V/I] means that the amino acid at this position may be a leucine (Leu, L), valine (Val, V) or isoleucine (Ile, I), and so forth for other combinations as described herein. Unless otherwise limited further, the amino acid X is defined such that it may be any of the 20 natural amino acids.

DETAILED DESCRIPTION OF THE INVENTION

The present invention is based on the surprising and inventive finding that expression of dispersins with a signal peptide from a bacterial alpha-amylase provides an improved yield of the dispersins compared to expression of the same dispersins with their native or other signal peptides. As can be seen from the Examples disclosed herein, use of the signal peptide from the *Bacillus licheniformis* alpha-amylase known as AmyL (SEQ ID NO: 2) provides an improved yield of at least two dispersins of the *Terribacillus* clade. Based on this observation, the present inventors expect a similar improvement for other dispersins, in particular other dispersins of the *Terribacillus* clade.

Nucleic Acid Constructs

In a first aspect, the present invention relates to a nucleic acid construct comprising:

a) a first polynucleotide encoding a signal peptide from a bacterial alpha-amylase; and b) a second polynucleotide encoding a polypeptide having hexosaminidase activity;

wherein the first polynucleotide and the second polynucleotide are operably linked in translational fusion.

The signal peptide may be from any bacterial alpha-amylase. Preferably, the signal peptide is from a Gram-positive alpha-amylase. More preferably, the signal peptide is from a *Bacillus* alpha-amylase. Even more preferably, the signal peptide is from a *Bacillus licheniformis* alpha-amylase. Most preferably, the signal peptide comprises or consists of SEQ ID NO: 2.

In some embodiments, the signal peptide is the AmyL signal peptide having an additional Ala at the C-terminus compared to SEQ ID NO: 2. In like manner, in some embodiments, the first poly-nucleotide encoding the signal peptide has an additional GCG codon at the 3' end of the signal pep-tide coding region compared to SEQ ID NO: 1.

It is expected that the invention will be just as effective when employing a signal peptide that is highly similar to the AmyL signal peptide disclosed in SEQ ID NO: 2 and encoded by SEQ ID NO: 1. One or more non-essential amino acids may, for example, be altered. Non-essential amino acids in a signal peptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the mole-cute, and the resultant molecules are tested for signal peptide activity to identify amino acid residues that are critical to the activity of the molecule and residues that are non-essential. See also, Hilton et al., 1996, J. Biol. Chem. 271: 4699-4708. The identity of essential and non-essential amino acids can also be inferred from an alignment with one or more related signal peptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO 95/17413; or WO 95/22625. Other methods that can be used include error-prone PCR, phage display (e.g. Low-man et al., 1991, Biochemistry 30: 10832-10837; U.S. Pat. No. 5,223,409; WO 92/06204), and region-directed mutagenesis (Derbyshire et al., 1986, Gene 46: 145; Ner et al., 1988, DNA 7: 127).

Mutagenesis/shuffling methods can be combined with high-throughput, automated screening methods to detect activity of cloned, mutagenized polypeptides expressed by host cells (Ness et al., 1999, Nature Biotechnology 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Thus, In a preferred embodiment, the signal peptide has a sequence identity of at least 80%, e.g. at least 85%, at least 90%, at least 91%, at least 92%, at least 93%, at least 94%, at least 95%, at least 96%, at least 97%, at least 98%, at least 99%, or 100%, to SEQ ID NO: 2; most preferably the signal peptide comprises, consists essentially of, or consists of SEQ ID NO: 2.

In a preferred embodiment, the polynucleotide encoding the signal peptide has a sequence identity of at least 80%, e.g. at least 85%, at least 90%, at least 91%, at least 92%, at least 93%, at least 94%, at least 95%, at least 96%, at least 97%, at least 98%, at least 99%, or 100%, to SEQ ID NO: 1; most preferably the polynucleotide comprises, consists essentially of, or consists of SEQ ID NO: 1.

In one aspect, the signal peptide is a variant (i.e., functional variant) or fragment (i.e., functional fragment) of the signal peptide of SEQ ID NO: 2. In one aspect, the number of alterations in the signal peptide variant of the present invention is 1-10, e.g., 1-5, such as 1, 2, 3, 4, or 5 alterations. Alterations includes substitutions, insertions, and/or deletions at one or more (e.g., several) positions compared to the parent. A substitution means replacement of the amino acid occupying a position with a different amino acid; a deletion means removal of the amino acid occupying a position; and an insertion means adding an amino acid adjacent to and immediately following the amino acid occupying a position.

In a preferred embodiment, the signal peptide is a variant of the mature polypeptide of SEQ ID NO: 2 comprising 1-10 alterations, e.g., 1-5, such as 1, 2, 3, 4, or 5 alterations, compared to SEQ ID NO: 2.

The polypeptide having hexosaminidase activity may be any such polypeptide or fragment or variant thereof. Polypeptides having hexosaminidase activity belong to the glycosyl hydrolase 20 (GH20, www.cazy.org) family of polypeptides. The GH20 family may be further subdivided into phylogenetic clades. More preferably, the polypeptide having hexosaminidase activity belong to the *Terribacillus* clade of the GH20 family.

The *Terribacillus* clade has been described in WO 2017/186943. The polypeptides belonging to this Glade share the WND domain (exemplified by the motif [VIM][LIV]G[GAV]DE[VI][PSA] provide as SEQ ID NO: 11 corresponding to positions 153-163 of the mature polypeptide of SEQ ID NO: 4, with G and DE corresponding to positions 158 and 160-161 of the mature polypeptide of SEQ ID NO: 4 being fully conserved in the *Terribacillus* clade and forming part of the active site), they are closely related in terms of sequence identity, and they share common functional features including deep cleaning properties in the presence of detergents. In view of the homogeneity of the *Terribacillus* clade, it is expected that the improved expression observed for two of its members will extend to all members of this Glade and likely also to other polypeptides having hexosaminidase activity that belong to different clades of the GH20 family.

Even more preferably, the polypeptide having hexosaminidase activity is from *Terribacillus saccharophilus*. Most preferably, the polypeptide having hexosaminidase activity comprises or consists of the mature polypeptide of SEQ ID NO: 4, SEQ ID NO:6 (corresponding to the mature polypeptide of SEQ ID NO: 4 with an additional C-terminal Ala), SEQ ID NO: 8, or SEQ ID NO: 10 (corresponding to the mature polypeptide of SEQ ID NO: 4 with an additional C-terminal Ala).

Similar and as described above in relation to the signal peptide, it is expected that the invention will be just as effective when employing a polypeptide having hexosaminidase activity that is highly similar to the mature polypeptide of SEQ ID NO: 4, SEQ ID NO: 6, SEQ ID NO: 8, or SEQ ID NO: 10 (encoded by SEQ ID NO: 3, SEQ ID NO: 5, SEQ ID NO: 7, and SEQ ID NO: 9, respectively).

Thus, in a preferred embodiment, the polypeptide having hexosaminidase activity has a sequence identity of at least 80%, e.g. at least 85%, at least 90%, at least 91%, at least 92%, at least 93%, at least 94%, at least 95%, at least 96%, at least 97%, at least 98%, at least 99%, or 100%, to the mature polypeptide of SEQ ID NO: 4, SEQ ID NO: 6, or SEQ ID NO: 8, or SEQ ID NO: 10; most preferably the polypeptide having hexosaminidase activity comprises, consists essentially of, or consists of the mature polypeptide of SEQ ID NO: 4, SEQ ID NO: 6, SEQ ID NO: 8, or SEQ ID NO: 10.

In a particularly preferred embodiment, the polypeptide having hexosaminidase activity has a sequence identity of at least 80%, e.g. at least 85%, at least 90%, at least 91%, at least 92%, at least 93%, at least 94%, at least 95%, at least 96%, at least 97%, at least 98%, at least 99%, or 100%, to the mature polypeptide of SEQ ID NO: 4 or SEQ ID NO: 8; most preferably the polypeptide having hexosaminidase activity comprises, consists essentially of, or consists of the mature polypeptide of SEQ ID NO: 4 or SEQ ID NO: 8.

In another particularly preferred embodiment, the polypeptide having hexosaminidase activity has a sequence identity of at least 80%, e.g. at least 85%, at least 90%, at least 91%, at least 92%, at least 93%, at least 94%, at least 95%, at least 96%, at least 97%, at least 98%, at least 99%, or 100%, to the mature polypeptide of SEQ ID NO: 6 or SEQ ID NO: 10; most preferably the polypeptide having hexosaminidase activity comprises, consists essentially of, or consists of the mature polypeptide of SEQ ID NO: 6 or SEQ ID NO: 10.

In one aspect, the polypeptide having hexosaminidase activity is a variant (i.e., functional variant) or fragment (i.e., functional fragment) of the mature polypeptide of SEQ ID NO: 4, SEQ ID NO: 6, SEQ ID NO: 8, or SEQ ID NO: 10.

In one aspect, the number of alterations in the variants of the present invention is 1-20, e.g. 1-10 and 1-5, such as 1, 2, 3, 4, 5, 6, 7, 8, 9 or 10 alterations. Alterations includes substitutions, insertions, and/or deletions at one or more (e.g. several) positions compared to the parent. A substitution means replacement of the amino acid occupying a position with a different amino acid; a deletion means removal of the amino acid occupying a position; and an insertion means adding an amino acid adjacent to and immediately following the amino acid occupying a position.

In a preferred embodiment, the polypeptide having hexosaminidase activity is a variant of the mature polypeptide of SEQ ID NO: 4 comprising 1-20 alterations, e.g. 1-10 and 1-5, such as 1, 2, 3, 4, 5, 6, 7, 8, 9 or 10 alterations, compared to SEQ ID NO: 4.

In a preferred embodiment, the polypeptide having hexosaminidase activity is a variant of the mature polypeptide of SEQ ID NO: 6 comprising 1-20 alterations, e.g. 1-10 and 1-5, such as 1, 2, 3, 4, 5, 6, 7, 8, 9 or 10 alterations, compared to SEQ ID NO: 6.

In a preferred embodiment, the polypeptide having hexosaminidase activity is a variant of the mature polypeptide of SEQ ID NO: 8 comprising 1-20 alterations, e.g. 1-10 and 1-5, such as 1, 2, 3, 4, 5, 6, 7, 8, 9 or 10 alterations, compared to SEQ ID NO: 8.

In a preferred embodiment, the polypeptide having hexosaminidase activity is a variant of the mature polypeptide of SEQ ID NO: 10 comprising 1-20 alterations, e.g. 1-10 and 1-5, such as 1, 2, 3, 4, 5, 6, 7, 8, 9 or 10 alterations, compared to SEQ ID NO: 10.

Due to the degeneracy of the genetic code, different polynucleotides can encode the same polypeptide. Thus, in a preferred embodiment, the polynucleotide encoding the polypeptide having hexosaminidase activity has a sequence identity of at least 80%, e.g. at least 85%, at least 90%, at least 91%, at least 92%, at least 93%, at least 94%, at least 95%, at least 96%, at least 97%, at least 98%, at least 99%, or 100%, to the mature polypeptide coding sequence of SEQ ID NO: 3, SEQ ID NO: 5, SEQ ID NO: 7, or SEQ ID NO: 9; most preferably the polynucleotide comprises, consists essentially of, or consists of the mature polypeptide coding sequence of SEQ ID NO: 3, SEQ ID NO: 5, SEQ ID NO: 7, or SEQ ID NO: 9.

In a particularly preferred embodiment, the polynucleotide encoding the polypeptide having hexosaminidase activity has a sequence identity of at least 80%, e.g. at least 85%, at least 90%, at least 91%, at least 92%, at least 93%, at least 94%, at least 95%, at least 96%, at least 97%, at least 98%, at least 99%, or 100%, to the mature polypeptide coding sequence of SEQ ID NO: 3 or SEQ ID NO: 7; most preferably the polynucleotide comprises, consists essentially of, or consists of the mature polypeptide coding sequence of SEQ ID NO: 3 or SEQ ID NO: 7.

In a particularly preferred embodiment, the polynucleotide encoding the polypeptide having hexosaminidase activity has a sequence identity of at least 80%, e.g. at least 85%, at least 90%, at least 91%, at least 92%, at least 93%, at least 94%, at least 95%, at least 96%, at least 97%, at least 98%, at least 99%, or 100%, to the mature polypeptide coding sequence of SEQ ID NO: 5 or SEQ ID NO: 9; most preferably the polynucleotide comprises, consists essentially of, or consists of the mature polypeptide coding sequence of SEQ ID NO: 5 or SEQ ID NO: 9.

The first and second polynucleotide are operably linked in translational fusion. In the context of the present invention, the term "operably linked in translation fusion" means that the signal peptide encoded by the first polynucleotide and the polypeptide having hexosaminidase activity encoded by the second polynucleotide are encoded in frame and translated together as a single polypeptide. Following translation, the signal peptide is removed to provide the mature polypeptide having hexosaminidase activity.

The first and second polynucleotide may be manipulated in a variety of ways to provide for expression of a variant. Manipulation of the polynucleotide prior to its insertion into a nucleic acid construct or expression vector may be desirable or necessary depending on the construct or vector. The techniques for modifying polynucleotides utilizing recombinant DNA methods are well known in the art.

Besides a signal peptide, the nucleic acid constructs of the invention may be operably linked to one or more further control sequences that direct the expression of the coding sequence in a suitable host cell under conditions compatible with the control sequences.

The control sequence may be a promoter, a polynucleotide recognized by a host cell for expression of a polynucleotide encoding a variant of the present invention. The promoter contains transcriptional control sequences that mediate the expression of the variant. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xyIA and xyIB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

In an embodiment, the promoter is a heterologous promoter. Preferably, the promoter is a tandem promoter. More preferably, the promoter is the cryIIIA promoter or a cryIIIA-based promoter. Even more preferably, the promoter is a tandem promoter comprising or derived from the cryIIIA promoter. Most preferably, the promoter comprises of consists of the cryIIIA promoter.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

In one embodiment, the promoter is a tandem promoter operably linked to an mRNA stabilizer region. Preferably, the mRNA stabilizer region is the cryIIIA mRNA stabilizer region.

The control sequence may also be a transcription terminator, which is recognized by a host cell to terminate transcription. The terminator is operably linked to the 3'-terminus of the polynucleotide encoding the variant. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

The control sequence may also be a propeptide coding sequence that encodes a propeptide positioned at the N-terminus of a variant. The resultant polypeptide is known as a proenzyme or propolypeptide (or a zymogen in some cases). A propolypeptide is generally inactive and can be converted to an active variant by catalytic or autocatalytic cleavage of the propeptide from the propolypeptide. The propeptide coding sequence may be obtained from the genes for *Bacillus subtilis* alkaline protease (aprE) or *Bacillus subtilis* neutral protease (nprT).

Where both signal peptide and propeptide sequences are present, the propeptide sequence is positioned next to the N-terminus of a variant and the signal peptide sequence is positioned next to the N-terminus of the propeptide sequence.

It may also be desirable to add regulatory sequences that regulate expression of the variant relative to the growth of the host cell. Examples of regulatory sequences are those that cause expression of the gene to be turned on or off in response to a chemical or physical stimulus, including the presence of a regulatory compound. Regulatory sequences in bacterial systems include the lac, tac, and trp operator systems.

Expression Vectors

The present invention also relates to recombinant expression vectors comprising a polynucleotide encoding a variant of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g. a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g. a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance.

The vector preferably contains an element(s) that permits integration of the vector into the host cell's genome or autonomous replication of the vector in the cell independent of the genome.

For integration into the host cell genome, the vector may rely on the polynucleotide's sequence encoding the variant or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

More than one copy of the first and second polynucleotide of the present invention may be inserted into a host cell to increase production of a variant. An increase in the copy number of the first and second polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g. Sambrook et al., 1989, supra).

Host Cells

The present invention also relates to recombinant host cells comprising a nucleic acid construct of the invention. A construct or vector comprising the construct is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the polynucleotide encoding the polypeptide having hexosaminidase acitivity and its source.

The host cell may be any cell useful in the recombinant production of a polypeptide having hexosaminidase acitivity. Preferably, the host cell is a bacterial host cell.

The bacterial host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells. Preferably, the bacterial host cell is *Bacillus licheniformis* or *Bacillus subtilis*. Most preferably, the bacterial host cell is *Bacillus licheniformis*

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell, including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g. Chang and Cohen, 1979, *Mol. Gen. Genet.* 168: 111-115), competent cell transformation (see, e.g. Young and Spizizen, 1961, *J. Bacteriol.* 81: 823-829, or Dubnau and Davidoff-Abelson, 1971, *J. Mol. Biol.* 56: 209-221), electroporation (see, e.g. Shigekawa and Dower, 1988, *Biotechniques* 6: 742-751), or conjugation (see, e.g. Koehler and Thorne, 1987, *J. Bacteriol.* 169: 5271-5278). The introduction of DNA into an *E. coli* cell may be effected by protoplast transformation (see, e.g. Hanahan, 1983, *J. Mol. Biol.* 166: 557-580) or electroporation (see, e.g. Dower et al., 1988, *Nucleic Acids Res.* 16: 6127-6145). The introduction of DNA into a *Streptomyces* cell may be effected by protoplast transformation, electroporation (see, e.g. Gong et al., 2004, *Folia Microbiol.* (*Praha*) 49: 399-405), conjugation (see, e.g. Mazodier et al., 1989, *J. Bacteriol.* 171: 3583-3585), or transduction (see, e.g. Burke et al., 2001, *Proc. Natl. Acad. Sci.* USA 98: 6289-6294). The introduction of DNA into a *Pseudomonas* cell may be effected by electroporation (see, e.g. Choi et al., 2006, *J. Microbiol. Methods* 64: 391-397), or conjugation (see, e.g. Pinedo and Smets, 2005, *Appl. Environ. Microbiol.* 71: 51-57). The introduction of DNA into a *Streptococcus* cell may be effected by natural competence (see, e.g. Perry and Kuramitsu, 1981, *Infect. Immun.* 32: 1295-1297), protoplast transformation (see, e.g. Catt and Jollick, 1991, *Microbios* 68: 189-207), electroporation (see, e.g. Buckley et al., 1999, *Appl. Environ. Microbiol.* 65: 3800-3804), or conjugation (see, e.g. Clewell, 1981, *Microbiol. Rev.* 45: 409-436). However, any method known in the art for introducing DNA into a host cell can be used.

Methods of Production

The present invention also relates to methods of producing a variant, comprising (a) cultivating a host cell of the present invention under conditions conducive for production of the polypeptide having hexosaminidase activity; and optionally (b) recovering the polypeptide having hexosaminidase activity.

The recombinant host cells are cultivated in a nutrient medium suitable for production of the polypeptide having hexosaminidase activity using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g. in catalogues of the American Type Culture Collection). If the polypeptide having hexosaminidase activity is secreted into the nutrient medium, the polypeptide can be recovered directly from the medium. If the polypeptide is not secreted, it can be recovered from cell lysates.

The polypeptide having hexosaminidase activity may be detected using methods known in the art that are specific for hexosaminidase. These detection methods include, but are not limited to, use of specific antibodies, formation of an enzyme product, or disappearance of an enzyme substrate. For example, an enzyme assay may be used to determine the activity of the polypeptide having hexosaminidase activity.

The polypeptide having hexosaminidase activity may be recovered using methods known in the art. For example, the polypeptide having hexosaminidase activity may be recovered from the nutrient medium by conventional procedures including, but not limited to, collection, centrifugation, filtration, extraction, spray-drying, evaporation, or precipitation. In one aspect, the whole fermentation broth is recovered.

The polypeptide having hexosaminidase activity may be purified by a variety of procedures known in the art including, but not limited to, chromatography (e.g. ion exchange, affinity, hydrophobic, chromatofocusing, and size exclusion), electrophoretic procedures (e.g. preparative isoelectric focusing), differential solubility (e.g. ammonium sulfate precipitation), SDS-PAGE, or extraction (see, e.g. *Protein Purification*, Janson and Ryden, editors, VCH Publishers, New York, 1989) to obtain a substantially pure polypeptide.

In an alternative aspect, the polypeptide having hexosaminidase activity is not recovered, but rather a host cell of the present invention expressing the polypeptide having hexosaminidase activity is used as a source of the variant.

Fermentation Broth Formulations or Cell Compositions

The present invention also relates to a fermentation broth formulation or a cell composition comprising a polypeptide having hexosaminidase activity. The fermentation broth product further comprises additional ingredients used in the fermentation process, such as, for example, cells (including, the host cells containing the nucleic acid constructs of the present invention which are used to produce the polypeptide having hexosaminidase activity), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g. expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g. filamentous fungal cells) are removed, e.g. by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g. bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g. filamentous fungal cells) are grown to saturation, incubated under carbon-limiting conditions to allow protein synthesis. In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

EXAMPLES

Materials and Methods

Media

*Bacillus* strains were grown on LB agar (10 g/l Tryptone, 5 g/l yeast extract, 5 g/l NaCl, 15 g/l agar) plates, on Difco Tryptose Blood Agar Base plates, or in LB liquid medium (10 g/l Tryptone, 5 g/l yeast extract, 5 g/l NaCl).

To select for erythromycin resistance, agar media were supplemented with 1 μg/ml erythromycin and 25 μg/ml lincomycin, and liquid media were supplemented with 5 μg/ml erythromycin.

Spizizen I and Spizizen II media were used for preparation and transformation of competent *Bacillus subtilis* cells.

Spizizen I medium consists of 1× Spizizen salts (6 g/l $KH_2PO_4$, 14 g/l $K_2HPO_4$, 2 g/l $(NH_4)_2SO_4$, 1 g/l sodium citrate dihydrate, 0.2 g/l $MgSO_4 \cdot 7H_2O$, pH 7.0), 0.5% glucose, 0.1% yeast extract, and 0.02% casein hydrolysate.

Spizizen II medium consists of Spizizen I medium supplemented with 0.5 mM $CaCl_2$, and 2.5 mM $MgCl_2$.

Conjugation donor strains were supplemented with 100 μg/ml D-alanine.

Strains

*Bacillus subtilis* PP3724. This strain is the donor strain for conjugation of *Bacillus* strains as described in WO 1996/029418.

*Bacillus licheniformis* SJ1904: This strain is described in WO 2008/066931.

Molecular Biology Methods

Competent cells of *Bacillus subtilis* strains prepared and transformed according to the method described in Yasbin et al. (1973): Transformation and transfection in lysogenic strains of *Bacillus subtilis* 168. J. Bacteriol. 113, 540-548.

Conjugation of *Bacillus licheniformis* was performed essentially as described in WO 1996/029418.

Dispersin Activity Assay 1 (Automated Assay)

This method is used in conjunction with a Beckman Coulter Biomek FX and Biomek NX (Beckman Coulter, Inc, Brea CA, USA) and a Molecular Devices Spectra Max plate reader (San Jose CA, USA). Samples are diluted 100-fold in 20 mM MOPS buffer, 0.01% w/w Brij-35, pH7 (assay buffer) and placed in an empty 96-well plate. A purified sample of dispersin with a known concentration is also diluted appropriately with sample buffer and is added to an empty column of the same plate with the samples. The robot will then make an additional 3 and 9-fold dilution of the samples and standards and place 20 μl of each into a new 96-well plate. Samples/standards are then incubated with 200 μl of a 5 mM 4-methylumbelliferyl-N-acetyl-β-D-glucosaminide substrate (Sigma-Aldrich M2133) for period of 15 minutes at ambient temperature; the reaction is quenched with 50 μl of 4% NaOH prior to a fluorescent read at EX368 nm/Em448 nm. The sample concentrations are extrapolated from the generated standard curve.

Dispersin Activity Assay 2

For dispersin activity measurement, the prepared 384-well microtiter plate containing 5 μl samples was added 35 μl dispersin assay solution (45 mM citrate buffer pH 5 added 0.5 mg/ml p-nitrophenyl-N-acetyl-β-D-glucosaminide). The 384-well plate was then incubated at room temperature for 3 hours. After incubation, 40 μl stop solution (0.4 M $Na_2CO_3$) was added to the sample and absorbance at 405 nm was measured. The obtained activity values were corrected for the back-ground by subtraction of the absorbance measurement obtained for a reference without dispersin.

Example 1. Construction of *Bacillus licheniformis* Strain Expressing *Terribacillus saccharophilus* Dispersin 43 (Disp43) with its Native Signal Peptide Plasmid pMRT558 was constructed for insertion of a gene encoding Disp43 with its native signal peptide (designated by gene name Disp43nat) into the genome of a *Bacillus* host using the site-specific recombinase-mediated method described in WO 2018/077796. A map of pMRT558 is shown in FIG. 1, the DNA sequence encoding Disp43 with its native signal peptide is shown in SEQ ID NO: 3, and the corresponding amino acid sequence is shown in SEQ ID NO: 4. Plasmid pMRT558 comprises native Disp43 gene (including the native signal peptide) flanked upstream by the FRT-F recombination region and downstream by the FRT-F3 (WO 2018/077796). Plasmid pMRT558 was introduced into conjugation donor strain *Bacillus subtilis* PP3724 by transformation, resulting in strain PP3724/pMRT558.

Using conjugation donor strain PP3724/pMRT558, plasmid pMRT558 was introduced by conjugation into a derivative of *Bacillus licheniformis* SJ1904 comprising two chromosomal target sites for insertion of the plasmid and deletions in the genes encoding alkaline protease (aprL), Glu-specific protease (mprL), bacillopeptidase F (bprAB), minor extracellular serine proteases (epr and vpr), se-creted quality control protease (wprA) and intracellular serine protease (ispA). At each of the two chromosomal target sites of the *B. licheniformis* host is an expression cassette comprising a promoter followed by the cryIIIA mRNA stabilizer region, an FRT-F recombination site, a fluorescent marker gene and an FRT-F3 recombination site. The plasmid inserted into the *B. licheniformis* chromosome by site-specific recombination between the FRT-F or FRT-F3 sites on the plasmid, and FRT-F or FRT-F3 sites at the target chromosomal loci. The plasmid was then allowed to excise from the chromosome via homologous recombination between the FRT-F and FRT-F3 regions on the plasmid and in the target chromosomal locus by incubation at 34° C. in the absence of erythromycin selection. Integrants that had lost the plasmid were selected by screening for erythromycin sensitivity and loss of fluorescence marker phenotype. Integration of the SPaprHDisp43 gene was confirmed by PCR analysis. One *B. licheniformis* integrant with the SPaprHDisp43 gene inserted at two chromosomal loci was designated MaTa322.

Figure 2:
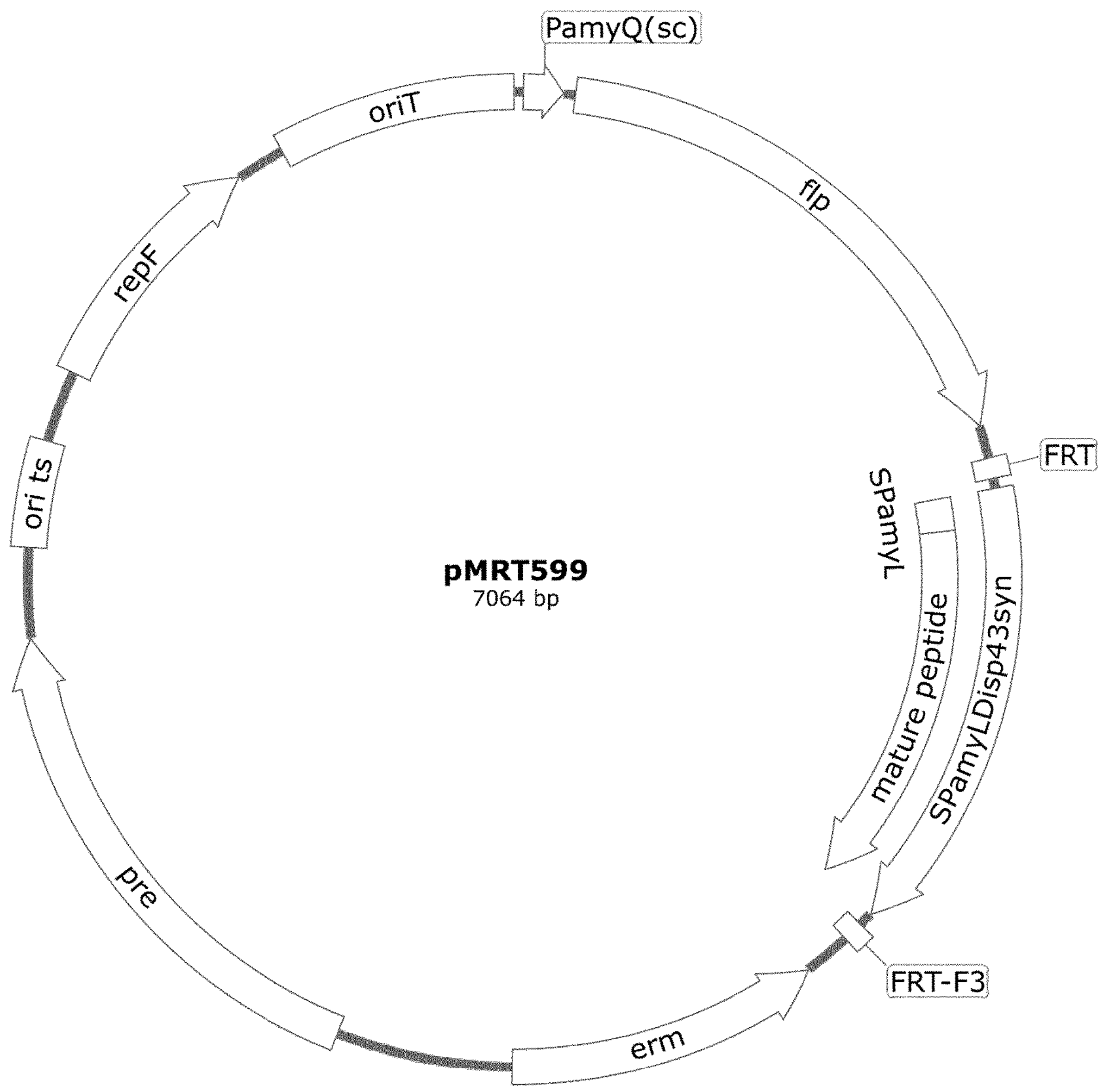
FIG. 2 shows a plasmid map of pMRT599.

Example 2. Construction of *Bacillus licheniformis* Strain Expressing *Terribacillus saccharophilus* Dispersin 43 (Disp43) with the amyL Signal Peptide Plasmid pMRT599 was constructed for insertion of a gene encoding Disp43 with the signal peptide from *B. licheniformis* alpha-amylase (amyL; designated by gene name SPamyLDisp43) into the genome of a *Bacillus* host using the site-specific recombinase-mediated method described in WO 2018/077796. A map of pMRT599 is shown in FIG. 2, the DNA sequence encoding Disp43 with the amyL signal peptide (including an additional GCG codon at the 3' end of the signal peptide coding region) is shown in SEQ ID NO: 5, and the corresponding amino acid sequence (including an additional Ala at the C-terminus of the signal peptide) shown in SEQ ID NO: 6. Plasmid pMRT599 comprises SPamyLDisp43 flanked upstream by the FRT-F recombination region and downstream by the FRT-F3 (WO 2018/077796). Plasmid pMRT599 was introduced into conjugation donor strain *Bacillus subtilis* PP3724 by transformation, resulting in strain PP3724/pMRT599.

Using conjugation donor strain PP3724/pMRT599, plasmid pMRT599 was introduced by conjugation into a derivative of *Bacillus licheniformis* SJ1904 comprising two chromosomal target sites for insertion of the plasmid and deletions in the genes encoding alkaline protease (aprL) and Gluspecific protease (mprL), bacillopeptidase F (bprAB), minor extracellular serine proteases (epr and vpr), secreted quality control protease (wprA) and intracellular serine protease (ispA). At each of the two chromosomal target sites of the *B. licheniformis* host is an expression cassette comprising a promoter followed by the cryIIIA mRNA stabilizer region, an FRT-F recombination site, a fluorescent marker gene and an FRT-F3 recombination site. The plasmid inserted into the *B. licheniformis* chromosome by site-specific recombination between the FRT-F or FRT-F3 sites on the plasmid, and FRT-F or FRT-F3 sites at the target chromosomal loci. The plasmid was then allowed to excise from the chromosome via homologous recombination between the FRT-F and FRT-F3 regions on the plasmid and in the target chromosomal locus by incubation at 34° C. in the absence of erythromycin selection. Integrants that had lost the plasmid were selected by screening for erythromycin sensitivity and loss of fluorescence marker phenotype. Integration of the SPaprHDisp43 gene was confirmed by PCR analysis. One *B. licheniformis* integrant with the SPaprHDisp43 gene inserted at two chromosomal loci was designated ATJI0058.

Figure 3:
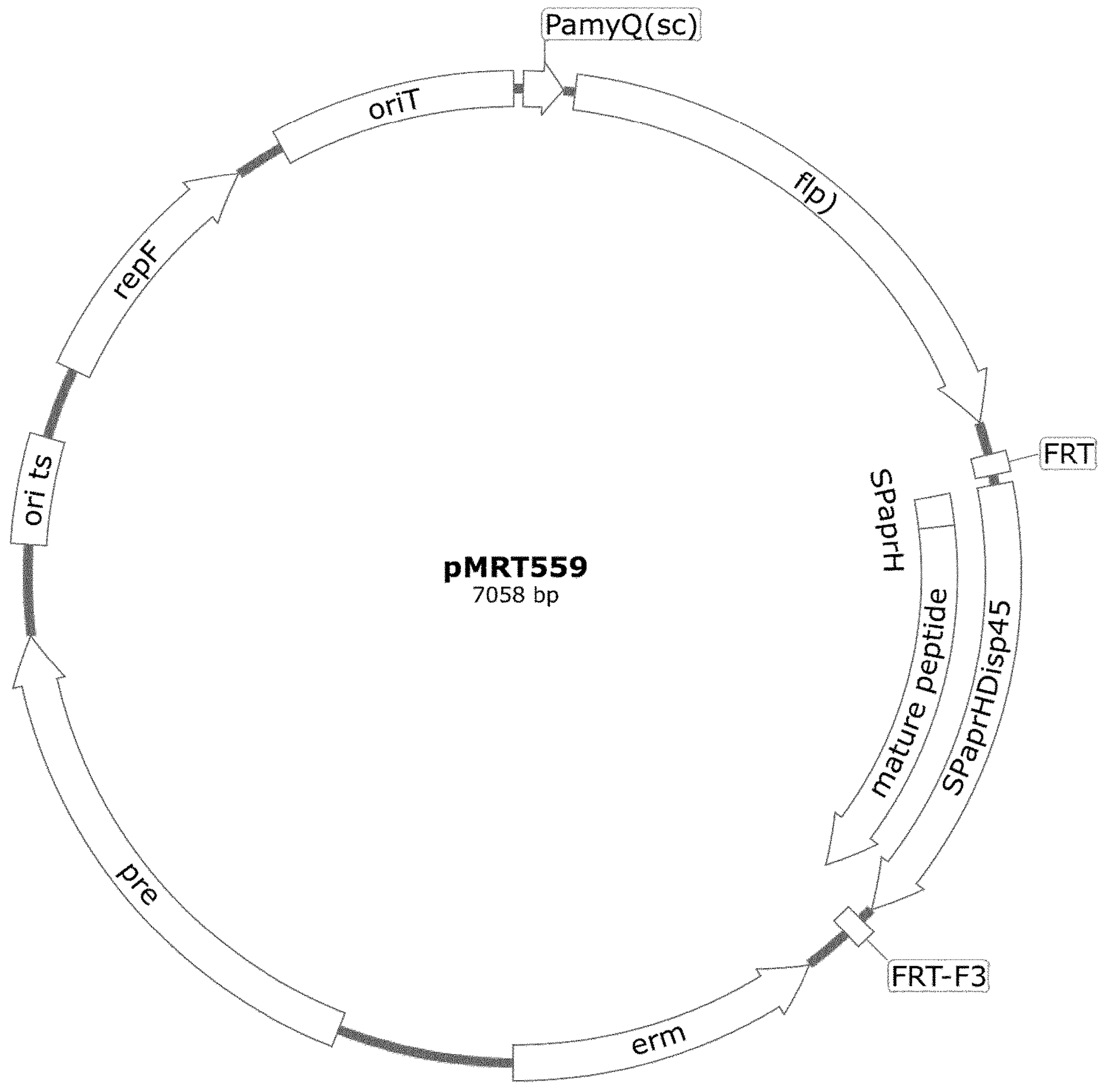
FIG. 3 shows a plasmid map of pMRT559.

Example 3. Construction of *Bacillus licheniformis* Strain Expressing *Terribacillus saccharophilus* Dispersin 45 (Disp45) with the aprH Signal Peptide Plasmid pMRT559 was constructed for insertion of a gene encoding Disp45 with the signal peptide from *B. clausii* alkaline protease (aprH; designated by gene name SPaprHDisp45) into the genome of a *Bacillus* host using the site-specific recombinase-mediated method described in WO 2018/077796. A map of pMRT559 is shown in FIG. 3, the DNA sequence encoding Disp45 with the aprH signal peptide is shown in SEQ ID NO: 7, and the corresponding amino acid sequence is shown in SEQ ID NO: 8. Plasmid pMRT559 comprises SPaprHDisp45 flanked upstream by the FRT-F recombination region and downstream by the FRT-F3 (WO 2018/077796). Plasmid pMRT559 was introduced into conjugation donor strain *Bacillus subtilis* PP3724 by transformation, resulting in strain PP3724/pMRT559.

Using conjugation donor strain PP3724/pMRT559, plasmid pMRT559 was introduced by conjugation into a derivative of *Bacillus licheniformis* SJ1904 comprising two chromosomal target sites for insertion of the plasmid and deletions in the genes encoding alkaline protease (aprL) and Glu-specific protease (mprL), bacillopeptidase F (bprAB), minor extracellular serine proteases (epr and vpr), secreted quality control protease (wprA) and intracellular serine protease (ispA). At each of the two chromosomal target sites of the *B. licheniformis* host is an expression cassette comprising a promoter followed by the cryIIIA mRNA stabilizer region, an FRT-F recombination site, a fluorescent marker gene and an FRT-F3 recombination site. The plasmid inserted into the *B. licheniformis* chromosome by site-specific recombination between the FRT-F or FRT-F3 sites on the plasmid, and FRT-F or FRT-F3 sites at the target chromosomal loci. The plasmid was then allowed to excise from the chromosome via homologous recombination between the FRT-F and FRT-F3 regions on the plasmid and in the target chromosomal locus by incubation at 34° C. in the absence of erythromycin selection. Integrants that had lost the plasmid were selected by screening for erythromycin sensitivity and loss of fluorescence marker phenotype. Integration of the SPaprHDisp45 gene was confirmed by PCR analysis. One *B. licheniformis* integrant with the SPaprHDisp45 gene inserted at two chromosomal loci was designated MaTa332.

Figure 4:
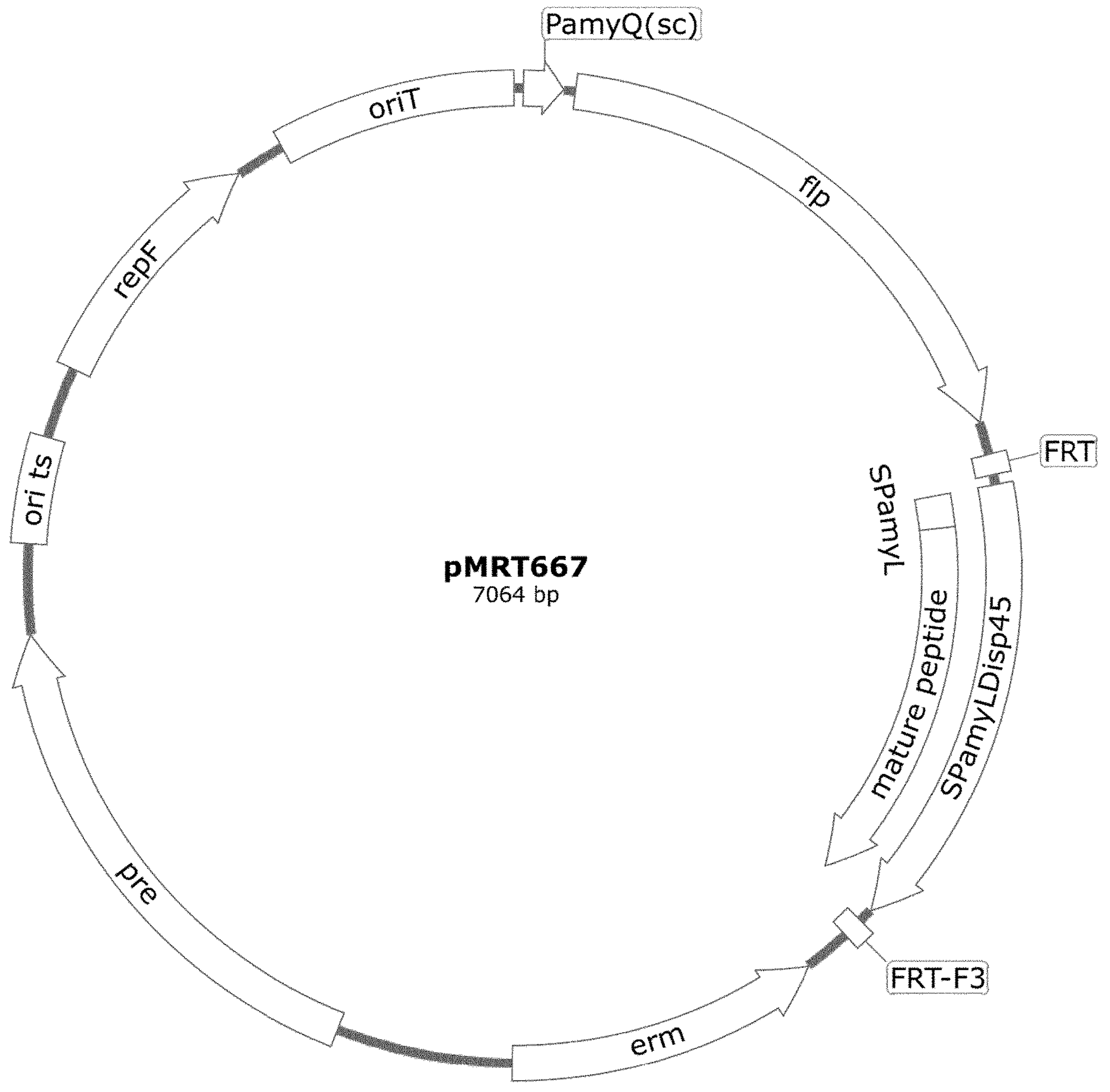
FIG. 4 shows a plasmid map of pMRT667.

Example 4. Construction of *Bacillus licheniformis* Strain Expressing *Terribacillus saccharophilus* Dispersin 45 (Disp45) with the amyL Signal Peptide Plasmid pMRT667 was constructed for insertion of a gene encoding Disp45 with the signal peptide from *B. licheniformis* alpha-amylase (amyL; designated by gene name SPamyLDisp45) into the genome of a *Bacillus* host using the site-specific recombinase-mediated method described in WO 2018/077796. A map of pMRT667 is shown in FIG. 4, the DNA sequence encoding Disp45 with the amyL signal peptide (including an additional GCG codon at the 3' end of the signal peptide coding region) is shown in SEQ ID NO: 9, and the corresponding amino acid sequence (including an additional Ala at the C-terminus of the signal peptide) is shown in SEQ ID NO: 10. Plasmid pMRT667 comprises SPamyLDisp45 flanked upstream by the FRT-F recombination region and downstream by the FRT-F3 (WO 2018/077796). Plasmid pMRT667 was introduced into conjugation donor strain *Bacillus subtilis* PP3724 by transformation, resulting in strain PP3724/pMRT667.

Using conjugation donor strain PP3724/pMRT667, plasmid pMRT667 was introduced by conjugation into a derivative of *Bacillus licheniformis* SJ1904 comprising two chromosomal target sites for insertion of the plasmid and deletions in the genes encoding alkaline protease (aprL) and Glu-specific protease (mprL), bacillopeptidase F (bprAB), minor extracellular serine proteases (epr and vpr), secreted quality control protease (wprA) and intracellular serine protease (ispA). At each of the two chromosomal target sites of the *B. licheniformis* host is an expression cassette comprising a promoter followed by the cryIIIA mRNA stabilizer region, an FRT-F recombination site, a fluorescent marker gene and an FRT-F3 recombination site. The plasmid inserted into the *B. licheniformis* chromosome by site-specific recombination between the FRT-F or FRT-F3 sites on the plasmid, and FRT-F or FRT-F3 sites at the target chromosomal loci. The plasmid was then allowed to excise from the chromosome via homologous recombination between the FRT-F and FRT-F3 regions on the plasmid and in the target chromosomal locus by incubation at 34° C. in the absence of erythromycin selection. Integrants that had lost the plasmid were selected by screening for erythromycin sensitivity and loss of fluorescence marker phenotype. Integration of the SPaprHDisp43 gene was confirmed by PCR analysis. One *B. licheniformis* integrant with the SPaprHDisp43 gene inserted at two chromosomal loci was designated MaTa366.

Example 5. Comparison of Disp43 Production by *Bacillus licheniformis* Integrants Expressing Disp43 with the Native and amyL Signal Peptides

*B. licheniformis* strains MaTa322 and ATJI0058 were cultivated, and Disp43 production by the strains was compared using enzyme activity assay. Relative total Disp43 product are shown in Table 1. Disp43 product was greater in ATJI0058 relative to MaTa322.

TABLE 1

Relative total Disp43 product for *B. licheniformis* strains expressing Disp43

| Strain | Number of Disp43 gene copies | Signal Peptide Source | Relative total product |
|---|---|---|---|
| MaTa322 | 2 | Native | 2.98 |
| ATJI0058 | 2 | amyL | 7.24 |

Example 6. Comparison of Disp45 Production by *Bacillus licheniformis* Integrants Expressing Disp45 with the aprH and amyL Signal Peptides

*B. licheniformis* strains MaTa326 and MaTa366 were cultivated, and Disp45 production by the strains was compared using enzyme activity assay. Relative total Disp45 product is shown in Table 2. Disp45 product was greater in MaTa366 relative to MaTa326.

TABLE 2

Relative total Disp45 product for *B. licheniformis* strains expressing Disp45

| Strain | Number of Disp45 gene copies | Signal Peptide Source | Relative total product |
|---|---|---|---|
| MaTa332 | 2 | aprH | 1.85 |
| MaTa366 | 2 | amyL | 8.58 |

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

List Of Embodiments

The invention is further defined by the following numbered embodiments:

[1] A nucleic acid construct comprising:

a) a first polynucleotide encoding a signal peptide from a bacterial alpha-amylase; and b) a second polynucleotide encoding a polypeptide having hexosaminidase activity;

wherein the first polynucleotide and the second polynucleotide are operably linked in translational fusion.

[2] The nucleic acid construct according to embodiment 1, wherein the nucleic acid construct further comprises a heterologous promoter, and wherein said promoter, the first polynucleotide, and the second polynucleotide are operably linked.

[3] The nucleic acid construct according to embodiment 2, wherein the promoter is the cryIIIA promoter or a cryIIIA-based promoter; preferably the heterologous promoter is a tandem promoter comprising the cryIIIA promoter or is a tandem promoter derived from the cryIIIA promoter.

[4] The nucleic acid construct according to embodiment 3, wherein the promoter is operably linked to an mRNA stabilizer region; preferably the mRNA stabilizer region is the cryIIIA mRNA stabilizer region

[5] The nucleic acid construct according to any of the preceding embodiments, wherein the signal peptide is a naturally occurring signal peptide, or a functional fragment or functional variant of a naturally occurring signal peptide.

[6] The nucleic acid construct according to any of the preceding embodiments, wherein the signal peptide is from an alpha-amylase expressed by a Gram-positive bacterium.

[7] The nucleic acid construct according to any of the preceding embodiments, wherein the signal peptide is from an alpha-amylase expressed by a *Bacillus* species; preferably the signal peptide is derived from an alpha-amylase expressed by a *Bacillus* species selected from the group consisting of *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis*; more preferably the signal peptide is derived from an alpha-amylase expressed by *Bacillus licheniformis* or *Bacillus subtilis*; most preferably the signal peptide is from an alpha-amylase expressed by *Bacillus licheniformis.*

[8] The nucleic acid construct according to any of the preceding embodiments, wherein the signal peptide is from the *B. licheniformis* alpha-amylase (AmyL).

[9] The nucleic acid construct according to any of the preceding embodiments, wherein the signal peptide has a sequence identity of at least 80%, e.g. at least 85%, at least 90%, at least 91%, at least 92%, at least 93%, at least 94%, at least 95%, at least 96%, at least 97%, at least 98%, at least 99%, or 100%, to SEQ ID NO: 2; preferably the signal peptide comprises, consists essentially of, or consists of SEQ ID NO: 2.

[10] The nucleic acid construct according to any of the preceding embodiments, wherein the polypeptide having hexosaminidase activity is a microbial polypeptide; preferably a bacterial polypeptide.

[11] The nucleic acid construct according to embodiment 10, wherein the polypeptide having hexosaminidase activity belongs to the *Terribacillus* clade and comprises the motif [VIM][LIV]G[GAV]DE[VI][PSA] (SEQ ID NO: 11).

[12] The nucleic acid construct according to any of embodiments 10-11, wherein the polypeptide having hexosaminidase activity is obtained from *Terribacillus saccharophilus.*

[13] The nucleic acid construct according to any of embodiments 10-12, wherein the polypeptide having hexosaminidase activity has a sequence identity of at least 80%, e.g. at least 85%, at least 90%, at least 91%, at least 92%, at least 93%, at least 94%, at least 95%, at least 96%, at least 97, at least 98%, at least 99%, or 100%, to the mature polypeptide of SEQ ID NO: 4, SEQ ID NO: 6, or SEQ ID NO: 8, or SEQ ID NO: 10.

[14] The nucleic acid construct according to any of embodiments 10-13, wherein the polypeptide having hexosaminidase activity comprises, consists essentially of, or consists of the mature polypeptide of SEQ ID NO: 4, SEQ ID NO: 6, SEQ ID NO: 8, or SEQ ID NO: 10.

[15] An expression vector comprising a nucleic acid construct comprising:

a) a first polynucleotide encoding a signal peptide from a bacterial alpha-amylase; and b) a second polynucleotide encoding a polypeptide having hexosaminidase activity; wherein the first polynucleotide and the second polynucleotide are operably linked in translational fusion.

[16] The expression vector according to embodiment 15, wherein the nucleic acid construct further comprises a heterologous promoter, and wherein said promoter, the first polynucleotide, and the second polynucleotide are operably linked.

[17] The expression vector according to embodiment 16, wherein the promoter is the cryIIIA promoter or a cryIIIA-based promoter; preferably the heterologous promoter is a tandem promoter comprising the cryIIIA promoter or is a tandem promoter derived from the cryIIIA promoter.

[18] The expression vector according to embodiment 17, wherein the promoter is operably linked to an mRNA stabilizer region; preferably the mRNA stabilizer region is the cryIIIA mRNA stabilizer region.

[19] The expression vector according to any of embodiments 15-18, wherein the signal peptide is a naturally occurring signal peptide, or a functional fragment or functional variant of a naturally occurring signal peptide.

[20] The expression vector according to any of embodiments 15-19, wherein the signal peptide is from an alpha-amylase expressed by a Gram-positive bacterium.

[21] The expression vector according to any of embodiments 15-20, wherein the signal peptide is from an alpha-amylase expressed by a *Bacillus* species; preferably the signal peptide is derived from an alpha-amylase expressed by a *Bacillus* species selected from the group consisting of *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells; more preferably the signal peptide is derived from an alpha-amylase expressed by *Bacillus licheniformis* or *Bacillus subtilis*; most preferably the signal peptide is from an alpha-amylase expressed by *Bacillus licheniformis.*

[22] The expression vector according to any of embodiments 15-21, wherein the signal peptide is from the *B. licheniformis* alpha-amylase (AmyL).

[23] The expression vector according to any of embodiments 15-22, wherein the signal peptide has a sequence identity of at least 80%, e.g. at least 85%, at least 90%, at least 91%, at least 92%, at least 93%, at least 94%, at least 95%, at least 96%, at least 97%, at least 98%, at least 99%, or 100%, to SEQ ID NO: 2; preferably the signal peptide comprises, consists essentially of, or consists of SEQ ID NO: 2.

[24] The expression vector according to any of embodiments 15-23, wherein the polypeptide having hexosaminidase activity is a microbial polypeptide; preferably a bacterial polypeptide.

[25] The expression vector according to embodiment 24, wherein the polypeptide having hexosaminidase activity belongs to the *Terribacillus* clade and comprises the motif [VIM][LIV]G[GAV]DE[VI][PSA] (SEQ ID NO: 11).

[26] The expression vector according to any of embodiments 24-25, wherein the polypeptide having hexosaminidase activity is obtained from *Terribacillus saccharophilus.*

[27] The expression vector according to any of embodiments 24-26, wherein the polypeptide having hexosaminidase activity has a sequence identity of at least 80%, e.g. at least 85%, at least 90%, at least 91%, at least 92%, at least 93%, at least 94%, at least 95%, at least 96%, at least 97, at least 98%, at least 99%, or 100%, to the mature polypeptide of SEQ ID NO: 4, SEQ ID NO: 6, or SEQ ID NO: 8, or SEQ ID NO: 10.

[28] The expression vector according to any of embodiments 24-27, wherein the polypeptide having hexosaminidase activity comprises, consists essentially of, or consists of the mature polypeptide of SEQ ID NO: 4, SEQ ID NO: 6, SEQ ID NO: 8, or SEQ ID NO: 10.

[29] A bacterial host cell comprising in its genome:

a) a nucleic acid construct comprising i) a first polynucleotide encoding a signal peptide from a bacterial alpha-amylase; and ii) a second polynucleotide encoding a polypeptide having hexosaminidase activity; wherein the first polynucleotide and the second polynucleotide are operably linked in translational fusion; and/or b) an expression vector comprising a nucleic acid construct comprising i) a first polynucleotide encoding a signal peptide from a bacterial alpha-amylase; and ii) a second polynucleotide encoding a polypeptide having hexosaminidase activity; wherein the first polynucleotide and the second polynucleotide are operably linked in translational fusion.

[30] The bacterial host cell of embodiment 29, wherein the bacterial host cell is a Gram-positive host cell.

[31] The bacterial host cell of any of embodiments 29-30, wherein the bacterial host cell is a *Bacillus* cell; preferably a *Bacillus* cell selected from the group consisting of *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cell; most preferably a *Bacillus licheniformis* cell.

[32] The bacterial host cell according to any of embodiments 29-31, wherein the nucleic acid construct further comprises a heterologous promoter, and wherein said promoter, the first polynucleotide, and the second polynucleotide are operably linked.

[33] The bacterial host cell according to embodiment 32, wherein the promoter is the cryIIIA promoter or a cryIIIA-based promoter; preferably the heterologous promoter is a tandem promoter comprising the cryIIIA promoter or is a tandem promoter derived from the cryIIIA promoter.

[34] The bacterial host cell according to embodiment 33, wherein the promoter is operably linked to an mRNA stabilizer region; preferably the mRNA stabilizer region is the cryIIIA mRNA stabilizer region.

[35] The bacterial host cell according to any of embodiments 29-34, wherein the signal peptide is a naturally occurring signal peptide, or a functional fragment or functional variant of a naturally occurring signal peptide.

[36] The bacterial host cell according to any of embodiments 29-35, wherein the signal peptide is from an alpha-amylase expressed by a Gram-positive bacterium.

[37] The bacterial host cell according to any of embodiments 29-36, wherein the signal peptide is from an alpha-amylase expressed by a *Bacillus* species; preferably the signal peptide is derived from an alpha-amylase expressed by a *Bacillus* species selected from the group consisting of *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis*; more preferably the signal peptide is derived from an alpha-amylase expressed by *Bacillus licheniformis* or *Bacillus subtilis*; most preferably the signal peptide is from an alpha-amylase expressed by *Bacillus licheniformis.*

[38] The bacterial host cell according to any of embodiments 29-37, wherein the signal peptide is from the *B. licheniformis* alpha-amylase (AmyL).

[39] The bacterial host cell according to any of embodiments 29-38, wherein the signal peptide has a sequence identity of at least 80%, e.g. at least 85%, at least 90%, at least 91%, at least 92%, at least 93%, at least 94%, at least 95%, at least 96%, at least 97%, at least 98%, at least 99%, or 100%, to SEQ ID NO: 2; preferably the signal peptide comprises, consists essentially of, or consists of SEQ ID NO: 2.

[40] The bacterial host cell according to any of embodiments 29-39, wherein the polypeptide having hexosaminidase activity is a microbial polypeptide; preferably a bacterial polypeptide.

[41] The bacterial host cell according to embodiment 40, wherein the polypeptide having hexosaminidase activity belongs to the *Terribacillus* clade and comprises the motif [VIM][LIV]G[GAV]DE[VI][PSA] (SEQ ID NO: 11).

[42] The bacterial host cell according to any of embodiments 40-41, wherein the polypeptide having hexosaminidase activity is obtained from *Terribacillus saccharophilus.*

[43] The bacterial host cell according to any of embodiments 40-42, wherein the polypeptide having hexosaminidase activity has a sequence identity of at least 80%, e.g. at least 85%, at least 90%, at 98%, at least 99%, or 100%, to the mature polypeptide of SEQ ID NO: 4, SEQ ID NO: 6, or SEQ ID NO: 8, or SEQ ID NO: 10.

[44] The bacterial host cell according to any of embodiments 40-43, wherein the polypeptide having hexosaminidase activity comprises, consists essentially of, or consists of the mature polypeptide of SEQ ID NO: 4, SEQ ID NO: 6, SEQ ID NO: 8, or SEQ ID NO: 10.

[45] A method of producing a polypeptide having hexosaminidase activity, the method comprising:

1) cultivating a bacterial host cell comprising in its genome:

a) a nucleic acid construct comprising i) a first polynucleotide encoding a signal peptide from a bacterial alpha-amylase; and ii) a second polynucleotide encoding a polypeptide having hexosaminidase activity; wherein the first polynucleotide and the second polynucleotide are operably linked in translational fusion; and/or b) an expression vector comprising a nucleic acid construct comprising i) a first polynucleotide encoding a signal peptide from a bacterial alpha-amylase; and ii) a second polynucleotide encoding a polypeptide having hexosaminidase activity; wherein the first polynucleotide and the second polynucleotide are operably linked in translational fusion; and optionally 2) recovering the polypeptide having hexosaminidase activity.

[46] The method of embodiment 45, wherein the bacterial host cell is a Gram-positive host cell.

[47] The method of any of embodiments 45-46, wherein the bacterial host cell is a *Bacillus* cell; preferably a *Bacillus* cell selected from the group consisting of *Bacillus alkalophilus, Bacillus amylolique faciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cell; most preferably a *Bacillus licheniformis* cell.

[48] The method according to any of embodiments 45-48, wherein the nucleic acid construct further comprises a heterologous promoter, and wherein said promoter, the first polynucleotide, and the second polynucleotide are operably linked.

[49] The method according to embodiment 48, wherein the promoter is the cryIIIA promoter or a cryIIIA-based promoter; preferably the heterologous promoter is a tandem promoter comprising the cryIIIA promoter or is a tandem promoter derived from the cryIIIA promoter.

[50] The method according to embodiment 48, wherein the promoter is operably linked to an mRNA stabilizer region; preferably the mRNA stabilizer region is the cryIIIA mRNA stabilizer region.

[51] The method according to any of embodiments 45-50, wherein the signal pep-tide is a naturally occurring signal peptide, or a functional fragment or functional variant of a naturally occurring signal peptide.

[52] The method according to any of embodiments 45-51, wherein the signal peptide is from an alphaamylase expressed by a Gram-positive bacterium.

[53] The method according to any of embodiments 45-52, wherein the signal peptide is from an alphaamylase expressed by a *Bacillus* species; preferably the signal peptide is derived from an alphaamylase expressed by a *Bacillus* species selected from the group consisting *of Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis*; more preferably the signal peptide is derived from an alpha-amylase expressed by *Bacillus licheniformis* or *Bacillus subtilis*; most preferably the signal peptide is from an alpha-amylase expressed by *Bacillus licheniformis*.

[54] The method according to any of embodiments 45-53, wherein the signal peptide is from the *B. licheniformis* alpha-amylase (AmyL).

[55] The method according to any of embodiments 45-54, wherein the signal peptide has a sequence identity of at least 80%, e.g. at least 85%, at least 90%, at least 91%, at least 92%, at least 93%, at least 94%, at least 95%, at least 96%, at least 97%, at least 98%, at least 99%, or 100%, to SEQ ID NO: 2; preferably the signal peptide comprises, consists essentially of, or consists of SEQ ID NO: 2.

[56] The method according to any of embodiments 45-55, wherein the polypeptide having hexosaminidase activity is a microbial polypeptide; preferably a bacterial polypeptide.

[57] The method according to embodiment 56, wherein the polypeptide having hexosaminidase activity belongs to the *Terribacillus* clade and comprises the motif [VIM][LIV]G[GAV]DE[VI][PSA] (SEQ ID NO: 11).

[58] The method according to any of embodiments 56-57, wherein the polypeptide having hexosaminidase activity is obtained from *Terribacillus saccharophilus*.

[59] The bacterial host cell according to any of embodiments 56-47, wherein the polypeptide having hexosaminidase activity has a sequence identity of at least 80%, e.g. at least 85%, at least 90%, at least 91%, at least 92%, at least 93%, at least 94%, at least 95%, at least 96%, at least 97, at least 98%, at least 99%, or 100%, to the mature polypeptide of SEQ ID NO: 4, SEQ ID NO: 6, or SEQ ID NO: 8, or SEQ ID NO: 10.

[60] The method according to any of embodiments 56-59, wherein the polypeptide having hexosaminidase activity comprises, consists essentially of, or consists of the mature polypeptide of SEQ ID NO: 4, SEQ ID NO: 6, SEQ ID NO: 8, or SEQ ID NO: 10.

The invention claimed is:

1. A nucleic acid construct comprising:

a) a first polynucleotide encoding a signal peptide from a bacterial alpha-amylase, wherein the signal peptide has a sequence identity of at least 90% to SEQ ID NO: 2; and b) a second polynucleotide encoding a polypeptide having hexosaminidase activity, wherein the polypeptide having hexosaminidase activity belongs to the *Terribacillus* clade and comprises the motif [VIM][LIV]G[GAV]DE[VI][PSA] (SEQ ID NO: 11);

wherein the signal peptide has an additional Ala at the C-terminus compared to SEQ ID NO: 2;

wherein the polypeptide having hexosaminidase activity has a sequence identity of at least 95% to the mature polypeptide of SEQ ID NO: 6 or SEQ ID NO: 10; and wherein the first polynucleotide and the second polynucleotide are operably linked in translational fusion.

2. The nucleic acid construct according to claim 1, wherein the nucleic acid construct further comprises a heterologous promoter, and wherein said promoter, the first polynucleotide, and the second polynucleotide are operably linked.

3. The nucleic acid construct according to claim 2, wherein the heterologous promoter is the cryIIIA promoter or a cryIIIA-based promoter.

4. The nucleic acid construct according to claim 1, wherein the signal peptide is a naturally occurring signal peptide, or a functional fragment or functional variant of a naturally occurring signal peptide.

5. The nucleic acid construct according to claim 1, wherein the signal peptide comprises or consists of SEQ ID NO: 2.

6. The nucleic acid construct according to claim 1, wherein the polypeptide having hexosaminidase activity is a microbial polypeptide.

7. The nucleic acid construct according to claim 1, wherein the polypeptide having hexosaminidase activity is a bacterial polypeptide.

8. The nucleic acid construct according to claim 1, wherein the polypeptide having hexosaminidase activity has a sequence identity of at least 97% to the mature polypeptide of SEQ ID NO: 6, or SEQ ID NO: 10.

9. The nucleic acid construct according to claim 1, wherein the polypeptide having hexosaminidase activity has a sequence identity of at least 99% to the mature polypeptide of SEQ ID NO: 6, or SEQ ID NO: 10.

10. The nucleic acid construct according to claim 1, wherein the polypeptide having hexosaminidase activity comprises or consists of the mature polypeptide of SEQ ID NO: 6, or SEQ ID NO: 10.

11. An expression vector comprising a nucleic acid construct according to claim 1.

12. A bacterial host cell comprising in its genome an expression vector according to claim 11.

13. The bacterial host cell of claim 12, wherein the bacterial host cell is a Gram-positive host cell.

14. The bacterial host cell of 12, wherein the bacterial host cell is a *Bacillus* cell.

15. The bacterial host cell of 12, wherein the bacterial host cell is a *Bacillus licheniformis* cell.

16. A method of producing a polypeptide having hexosaminidase activity, the method comprising:

a) cultivating a bacterial host cell according to claim 12 under conditions conducive for production of the polypeptide having hexosaminidase activity; and optionally b) recovering the polypeptide having hexosaminidase activity.

17. The nucleic acid construct according to claim 1, wherein the signal peptide is a variant of SEQ ID NO: 2 having two alterations compared to SEQ ID NO: 2.

18. The nucleic acid construct according to claim 1, wherein the signal peptide is a variant of SEQ ID NO: 2 having one alteration compared to SEQ ID NO: 2.

* * * * *

SEQUENCE LISTING

```
<160> NUMBER OF SEQ ID NOS: 11

<210> SEQ ID NO 1
<211> LENGTH: 81
<212> TYPE: DNA
<213> ORGANISM: Artificial Sequence
<220> FEATURE:
<223> OTHER INFORMATION: AmyL signal peptide coding sequence

<400> SEQUENCE: 1
```

```
atgaaacaac aaaaacggct ttacgcccga ttgctgacgc tgttatttgc gctcatcttc     60

ttgctgcctc attctgcagc a                                               81


<210> SEQ ID NO 2
<211> LENGTH: 27
<212> TYPE: PRT
<213> ORGANISM: Artificial Sequence
<220> FEATURE:
<223> OTHER INFORMATION: AmyL signal peptide

<400> SEQUENCE: 2

Met Lys Gln Gln Lys Arg Leu Tyr Ala Arg Leu Leu Thr Leu Leu Phe
1               5                   10                  15

Ala Leu Ile Phe Leu Leu Pro His Ser Ala Ala
            20                  25


<210> SEQ ID NO 3
<211> LENGTH: 1050
<212> TYPE: DNA
<213> ORGANISM: Terribacillus saccharophilus
<220> FEATURE:
<221> NAME/KEY: CDS
<222> LOCATION: (1)..(1047)
<220> FEATURE:
<221> NAME/KEY: sig_peptide
<222> LOCATION: (1)..(75)
<220> FEATURE:
<221> NAME/KEY: mat_peptide
<222> LOCATION: (76)..(1047)

<400> SEQUENCE: 3

atg ttg att aaa ttt ctt tct atc aca aca gtt agt ata ctc ttg ttt       48
Met Leu Ile Lys Phe Leu Ser Ile Thr Thr Val Ser Ile Leu Leu Phe
-25                 -20                 -15                 -10

cta acg atg gcg aat aca gca caa gca aag gat caa gag aaa gga att       96
Leu Thr Met Ala Asn Thr Ala Gln Ala Lys Asp Gln Glu Lys Gly Ile
                -5                  -1  1               5

aca atc gat att tcg aga aag tac tat tcc att ggt aca tta aaa gca      144
Thr Ile Asp Ile Ser Arg Lys Tyr Tyr Ser Ile Gly Thr Leu Lys Ala
        10                  15                  20

att gtt gac gag ata aac gct aat ggc gga gac tac ttg cag ctg cat      192
Ile Val Asp Glu Ile Asn Ala Asn Gly Gly Asp Tyr Leu Gln Leu His
    25                  30                  35

ttc tca gat aat gag agc tat gcg att gcc tct gaa ttc ctt ggt cag      240
Phe Ser Asp Asn Glu Ser Tyr Ala Ile Ala Ser Glu Phe Leu Gly Gln
40                  45                  50                  55

aac agt gaa aat cct aat tct act tac tta aca aaa aag gaa ctt tta      288
Asn Ser Glu Asn Pro Asn Ser Thr Tyr Leu Thr Lys Lys Glu Leu Leu
                60                  65                  70

tcg ctt ata gca tac agc aat gat aga aat ata atg gtt att cct gat      336
Ser Leu Ile Ala Tyr Ser Asn Asp Arg Asn Ile Met Val Ile Pro Asp
            75                  80                  85

att gat tta cca gcg cat tcc aag ggc tgg ctg aat gta atg aaa gag      384
Ile Asp Leu Pro Ala His Ser Lys Gly Trp Leu Asn Val Met Lys Glu
        90                  95                  100

aaa gat agt gga tta tat acg gac atc gta aca gat tat agt gaa gat      432
Lys Asp Ser Gly Leu Tyr Thr Asp Ile Val Thr Asp Tyr Ser Glu Asp
    105                 110                 115

aca ttg gat tat cac aat aat gca gct gcc ctg tat aca gca aac cag      480
Thr Leu Asp Tyr His Asn Asn Ala Ala Ala Leu Tyr Thr Ala Asn Gln
120                 125                 130                 135

cta ttg gac gaa gta ctt gat tta ttt tat cag cct aag ttc gca gga      528
```

```
Leu Leu Asp Glu Val Leu Asp Leu Phe Tyr Gln Pro Lys Phe Ala Gly
            140                 145                 150

aaa cag agg atc gta ctt ggc ggg gat gaa gtg ccg ggg agt gga gca      576
Lys Gln Arg Ile Val Leu Gly Gly Asp Glu Val Pro Gly Ser Gly Ala
            155                 160                 165

cat cag acg gat ttt atc cga ttt atg aat caa att gac gaa aca gct      624
His Gln Thr Asp Phe Ile Arg Phe Met Asn Gln Ile Asp Glu Thr Ala
        170                 175                 180

aaa gcc agc aat tat gaa ccg cag atg tgg aat gac agt att aca cca      672
Lys Ala Ser Asn Tyr Glu Pro Gln Met Trp Asn Asp Ser Ile Thr Pro
    185                 190                 195

gaa gga att caa aat ttg gat aga agt ttc tct atc ctt tat tgg aag      720
Glu Gly Ile Gln Asn Leu Asp Arg Ser Phe Ser Ile Leu Tyr Trp Lys
200                 205                 210                 215

caa agc aca ctc tca agc ggc gca cag ggt tta gat gta caa aat ttt      768
Gln Ser Thr Leu Ser Ser Gly Ala Gln Gly Leu Asp Val Gln Asn Phe
            220                 225                 230

gaa gaa aag ggt ttt tcg gta tat aac tat aat gcg tat tct tta tat      816
Glu Glu Lys Gly Phe Ser Val Tyr Asn Tyr Asn Ala Tyr Ser Leu Tyr
            235                 240                 245

ttc ctg cca tca act cgg ttt aca caa gaa gat ata aca gaa cag att      864
Phe Leu Pro Ser Thr Arg Phe Thr Gln Glu Asp Ile Thr Glu Gln Ile
        250                 255                 260

gac tat atg aaa tgg gct tac gca tat aat aag ttt ttc tac att tca      912
Asp Tyr Met Lys Trp Ala Tyr Ala Tyr Asn Lys Phe Phe Tyr Ile Ser
    265                 270                 275

gat tac tac aaa caa gtg gat act tct aac gtg aaa gga tcc agc tta      960
Asp Tyr Tyr Lys Gln Val Asp Thr Ser Asn Val Lys Gly Ser Ser Leu
280                 285                 290                 295

gtt ttt tgg ggc gaa cac gcc aat gac tta agc caa gag gga ttg ctt     1008
Val Phe Trp Gly Glu His Ala Asn Asp Leu Ser Gln Glu Gly Leu Leu
            300                 305                 310

gaa caa gag aag cct tta ata caa aat ttt ctt agc tta taa             1050
Glu Gln Glu Lys Pro Leu Ile Gln Asn Phe Leu Ser Leu
            315                 320


<210> SEQ ID NO 4
<211> LENGTH: 349
<212> TYPE: PRT
<213> ORGANISM: Terribacillus saccharophilus

<400> SEQUENCE: 4

Met Leu Ile Lys Phe Leu Ser Ile Thr Thr Val Ser Ile Leu Leu Phe
-25                 -20                 -15                 -10

Leu Thr Met Ala Asn Thr Ala Gln Ala Lys Asp Gln Glu Lys Gly Ile
            -5                  -1  1               5

Thr Ile Asp Ile Ser Arg Lys Tyr Tyr Ser Ile Gly Thr Leu Lys Ala
        10                  15                  20

Ile Val Asp Glu Ile Asn Ala Asn Gly Gly Asp Tyr Leu Gln Leu His
    25                  30                  35

Phe Ser Asp Asn Glu Ser Tyr Ala Ile Ala Ser Glu Phe Leu Gly Gln
40                  45                  50                  55

Asn Ser Glu Asn Pro Asn Ser Thr Tyr Leu Thr Lys Lys Glu Leu Leu
            60                  65                  70

Ser Leu Ile Ala Tyr Ser Asn Asp Arg Asn Ile Met Val Ile Pro Asp
            75                  80                  85

Ile Asp Leu Pro Ala His Ser Lys Gly Trp Leu Asn Val Met Lys Glu
        90                  95                  100
```

```
Lys Asp Ser Gly Leu Tyr Thr Asp Ile Val Thr Asp Tyr Ser Glu Asp
    105                 110                 115

Thr Leu Asp Tyr His Asn Asn Ala Ala Ala Leu Tyr Thr Ala Asn Gln
120                 125                 130                 135

Leu Leu Asp Glu Val Leu Asp Leu Phe Tyr Gln Pro Lys Phe Ala Gly
                140                 145                 150

Lys Gln Arg Ile Val Leu Gly Gly Asp Glu Val Pro Gly Ser Gly Ala
            155                 160                 165

His Gln Thr Asp Phe Ile Arg Phe Met Asn Gln Ile Asp Glu Thr Ala
        170                 175                 180

Lys Ala Ser Asn Tyr Glu Pro Gln Met Trp Asn Asp Ser Ile Thr Pro
    185                 190                 195

Glu Gly Ile Gln Asn Leu Asp Arg Ser Phe Ser Ile Leu Tyr Trp Lys
200                 205                 210                 215

Gln Ser Thr Leu Ser Ser Gly Ala Gln Gly Leu Asp Val Gln Asn Phe
                220                 225                 230

Glu Glu Lys Gly Phe Ser Val Tyr Asn Tyr Asn Ala Tyr Ser Leu Tyr
            235                 240                 245

Phe Leu Pro Ser Thr Arg Phe Thr Gln Glu Asp Ile Thr Glu Gln Ile
        250                 255                 260

Asp Tyr Met Lys Trp Ala Tyr Ala Tyr Asn Lys Phe Phe Tyr Ile Ser
    265                 270                 275

Asp Tyr Tyr Lys Gln Val Asp Thr Ser Asn Val Lys Gly Ser Ser Leu
280                 285                 290                 295

Val Phe Trp Gly Glu His Ala Asn Asp Leu Ser Gln Glu Gly Leu Leu
                300                 305                 310

Glu Gln Glu Lys Pro Leu Ile Gln Asn Phe Leu Ser Leu
            315                 320
```

<210> SEQ ID NO 5
<211> LENGTH: 1062
<212> TYPE: DNA
<213> ORGANISM: Artificial Sequence
<220> FEATURE:
<223> OTHER INFORMATION: SPamyLDisp43syn coding sequence
<220> FEATURE:
<221> NAME/KEY: CDS
<222> LOCATION: (1)..(1059)
<220> FEATURE:
<221> NAME/KEY: sig_peptide
<222> LOCATION: (1)..(84)
<220> FEATURE:
<221> NAME/KEY: mat_peptide
<222> LOCATION: (85)..(1059)

<400> SEQUENCE: 5

```
atg aaa caa caa aaa cgg ctt tac gcc cga ttg ctg acg ctg tta ttt       48
Met Lys Gln Gln Lys Arg Leu Tyr Ala Arg Leu Leu Thr Leu Leu Phe
            -25                 -20                 -15

gcg ctc atc ttc ttg ctg cct cat tct gca gca gcg gcg aaa gat caa       96
Ala Leu Ile Phe Leu Leu Pro His Ser Ala Ala Ala Ala Lys Asp Gln
        -10                 -5              -1  1

gaa aaa ggc atc acg atc gat atc agc cgc aaa tat tac agc atc ggc      144
Glu Lys Gly Ile Thr Ile Asp Ile Ser Arg Lys Tyr Tyr Ser Ile Gly
5                   10                  15                  20

acg ctg aaa gcg atc gtc gat gaa atc aac gcg aat ggc gga gat tat      192
Thr Leu Lys Ala Ile Val Asp Glu Ile Asn Ala Asn Gly Gly Asp Tyr
                25                  30                  35

ctg caa ctg cat ttt agc gat aac gaa agc tat gcg atc gcg agc gaa      240
Leu Gln Leu His Phe Ser Asp Asn Glu Ser Tyr Ala Ile Ala Ser Glu
```

```
            40                  45                  50

ttt ctg ggc caa aac agc gaa aac ccg aac agc acg tat ctg acg aaa      288
Phe Leu Gly Gln Asn Ser Glu Asn Pro Asn Ser Thr Tyr Leu Thr Lys
        55                  60                  65

aaa gaa ctg ctg agc ctg atc gcg tat agc aac gat cgc aac atc atg      336
Lys Glu Leu Leu Ser Leu Ile Ala Tyr Ser Asn Asp Arg Asn Ile Met
    70                  75                  80

gtc atc ccg gac atc gat ctt ccg gca cat agc aaa ggc tgg ctg aac      384
Val Ile Pro Asp Ile Asp Leu Pro Ala His Ser Lys Gly Trp Leu Asn
85                  90                  95                  100

gtc atg aaa gaa aaa gat agc gga ctg tat acg gat atc gtc acg gat      432
Val Met Lys Glu Lys Asp Ser Gly Leu Tyr Thr Asp Ile Val Thr Asp
                105                 110                 115

tat agc gaa gat acg ctg gac tat cat aac aat gcg gca gcg ctt tat      480
Tyr Ser Glu Asp Thr Leu Asp Tyr His Asn Asn Ala Ala Ala Leu Tyr
            120                 125                 130

acg gcg aac caa ctg ctg gat gaa gtc ctg gac ctg ttt tat caa ccg      528
Thr Ala Asn Gln Leu Leu Asp Glu Val Leu Asp Leu Phe Tyr Gln Pro
        135                 140                 145

aaa ttt gcg gga aaa caa cgc atc gtc ctt gga ggc gac gaa gtc cct      576
Lys Phe Ala Gly Lys Gln Arg Ile Val Leu Gly Gly Asp Glu Val Pro
    150                 155                 160

ggc agc gga gcg cat caa acg gat ttt atc cgc ttt atg aac cag atc      624
Gly Ser Gly Ala His Gln Thr Asp Phe Ile Arg Phe Met Asn Gln Ile
165                 170                 175                 180

gat gaa acg gcg aaa gcg agc aac tat gaa ccg caa atg tgg aat gat      672
Asp Glu Thr Ala Lys Ala Ser Asn Tyr Glu Pro Gln Met Trp Asn Asp
                185                 190                 195

agc atc aca ccg gaa ggc atc caa aac ctg gat cgc agc ttt agc atc      720
Ser Ile Thr Pro Glu Gly Ile Gln Asn Leu Asp Arg Ser Phe Ser Ile
            200                 205                 210

ctg tat tgg aaa caa agc acg ctg tca agc gga gcc caa ggc ctg gat      768
Leu Tyr Trp Lys Gln Ser Thr Leu Ser Ser Gly Ala Gln Gly Leu Asp
        215                 220                 225

gtc caa aac ttt gaa gaa aag ggc ttt agc gtc tat aac tat aat gcg      816
Val Gln Asn Phe Glu Glu Lys Gly Phe Ser Val Tyr Asn Tyr Asn Ala
    230                 235                 240

tac agc ctg tac ttt ctg ccg agc acg cgc ttt acg caa gaa gat atc      864
Tyr Ser Leu Tyr Phe Leu Pro Ser Thr Arg Phe Thr Gln Glu Asp Ile
245                 250                 255                 260

acg gaa caa atc gac tat atg aaa tgg gcg tat gcg tac aac aag ttc      912
Thr Glu Gln Ile Asp Tyr Met Lys Trp Ala Tyr Ala Tyr Asn Lys Phe
                265                 270                 275

ttt tat atc agc gac tac tac aaa cag gtc gat acg agc aac gtc aaa      960
Phe Tyr Ile Ser Asp Tyr Tyr Lys Gln Val Asp Thr Ser Asn Val Lys
            280                 285                 290

ggc agc agc ctg gtc ttt tgg gga gaa cat gcg aac gat ctg agc caa     1008
Gly Ser Ser Leu Val Phe Trp Gly Glu His Ala Asn Asp Leu Ser Gln
        295                 300                 305

gaa ggc ctg ctg gaa caa gaa aaa ccg ctg atc caa aat ttt ctg agc     1056
Glu Gly Leu Leu Glu Gln Glu Lys Pro Leu Ile Gln Asn Phe Leu Ser
    310                 315                 320

ctg taa                                                             1062
Leu
325
```

<210> SEQ ID NO 6
<211> LENGTH: 353
<212> TYPE: PRT
<213> ORGANISM: Artificial Sequence

```
<220> FEATURE:
<223> OTHER INFORMATION: Synthetic Construct

<400> SEQUENCE: 6

Met Lys Gln Gln Lys Arg Leu Tyr Ala Arg Leu Leu Thr Leu Leu Phe
            -25                 -20                 -15

Ala Leu Ile Phe Leu Leu Pro His Ser Ala Ala Ala Ala Lys Asp Gln
        -10                 -5                  -1  1

Glu Lys Gly Ile Thr Ile Asp Ile Ser Arg Lys Tyr Tyr Ser Ile Gly
5                   10                  15                  20

Thr Leu Lys Ala Ile Val Asp Glu Ile Asn Ala Asn Gly Gly Asp Tyr
                25                  30                  35

Leu Gln Leu His Phe Ser Asp Asn Glu Ser Tyr Ala Ile Ala Ser Glu
            40                  45                  50

Phe Leu Gly Gln Asn Ser Glu Asn Pro Asn Ser Thr Tyr Leu Thr Lys
        55                  60                  65

Lys Glu Leu Leu Ser Leu Ile Ala Tyr Ser Asn Asp Arg Asn Ile Met
    70                  75                  80

Val Ile Pro Asp Ile Asp Leu Pro Ala His Ser Lys Gly Trp Leu Asn
85                  90                  95                  100

Val Met Lys Glu Lys Asp Ser Gly Leu Tyr Thr Asp Ile Val Thr Asp
                105                 110                 115

Tyr Ser Glu Asp Thr Leu Asp Tyr His Asn Asn Ala Ala Ala Leu Tyr
            120                 125                 130

Thr Ala Asn Gln Leu Leu Asp Glu Val Leu Asp Leu Phe Tyr Gln Pro
        135                 140                 145

Lys Phe Ala Gly Lys Gln Arg Ile Val Leu Gly Gly Asp Glu Val Pro
    150                 155                 160

Gly Ser Gly Ala His Gln Thr Asp Phe Ile Arg Phe Met Asn Gln Ile
165                 170                 175                 180

Asp Glu Thr Ala Lys Ala Ser Asn Tyr Glu Pro Gln Met Trp Asn Asp
                185                 190                 195

Ser Ile Thr Pro Glu Gly Ile Gln Asn Leu Asp Arg Ser Phe Ser Ile
            200                 205                 210

Leu Tyr Trp Lys Gln Ser Thr Leu Ser Ser Gly Ala Gln Gly Leu Asp
        215                 220                 225

Val Gln Asn Phe Glu Glu Lys Gly Phe Ser Val Tyr Asn Tyr Asn Ala
    230                 235                 240

Tyr Ser Leu Tyr Phe Leu Pro Ser Thr Arg Phe Thr Gln Glu Asp Ile
245                 250                 255                 260

Thr Glu Gln Ile Asp Tyr Met Lys Trp Ala Tyr Ala Tyr Asn Lys Phe
                265                 270                 275

Phe Tyr Ile Ser Asp Tyr Tyr Lys Gln Val Asp Thr Ser Asn Val Lys
            280                 285                 290

Gly Ser Ser Leu Val Phe Trp Gly Glu His Ala Asn Asp Leu Ser Gln
        295                 300                 305

Glu Gly Leu Leu Glu Gln Glu Lys Pro Leu Ile Gln Asn Phe Leu Ser
    310                 315                 320

Leu
325


<210> SEQ ID NO 7
<211> LENGTH: 1056
<212> TYPE: DNA
<213> ORGANISM: Artificial Sequence
```

```
<220> FEATURE:
<223> OTHER INFORMATION: SPaprHDisp45 coding sequence
<220> FEATURE:
<221> NAME/KEY: CDS
<222> LOCATION: (1)..(1053)
<220> FEATURE:
<221> NAME/KEY: sig_peptide
<222> LOCATION: (1)..(81)
<220> FEATURE:
<221> NAME/KEY: mat_peptide
<222> LOCATION: (82)..(1053)

<400> SEQUENCE: 7

atg aag aaa ccg ttg ggg aaa att gtc gca agc acc gca cta ctc att       48
Met Lys Lys Pro Leu Gly Lys Ile Val Ala Ser Thr Ala Leu Leu Ile
        -25                 -20                 -15

tct gtt gct ttt agt tca tcg ata gca tcg gct cag gac cag gag aag       96
Ser Val Ala Phe Ser Ser Ser Ile Ala Ser Ala Gln Asp Gln Glu Lys
    -10                 -5              -1  1               5

ggc atc acg atc gac atc tca cgc aag cac tac acg gtt gag acg ctt      144
Gly Ile Thr Ile Asp Ile Ser Arg Lys His Tyr Thr Val Glu Thr Leu
                10                  15                  20

aag tca ctt gtt gac gag atc tca tac aat ggt ggc aac tac gtt cag      192
Lys Ser Leu Val Asp Glu Ile Ser Tyr Asn Gly Gly Asn Tyr Val Gln
            25                  30                  35

ctt cac ttc tct gac aac gag aac tac gcg atc gcg tca gag tac ctt      240
Leu His Phe Ser Asp Asn Glu Asn Tyr Ala Ile Ala Ser Glu Tyr Leu
        40                  45                  50

ggc caa tca tct gag aac acg aac aac acg tac ctt acg aag aac gag      288
Gly Gln Ser Ser Glu Asn Thr Asn Asn Thr Tyr Leu Thr Lys Asn Glu
    55                  60                  65

ctt ctt tca ctt atc gcg tac tct aac gac aag gac atc ctt gtt atc      336
Leu Leu Ser Leu Ile Ala Tyr Ser Asn Asp Lys Asp Ile Leu Val Ile
70                  75                  80                  85

cct gac atc gac ctt cct gcg cac tct aag ggc tgg ctt gag ctt atc      384
Pro Asp Ile Asp Leu Pro Ala His Ser Lys Gly Trp Leu Glu Leu Ile
                90                  95                  100

aag aag aag gac gtt aaa ctt tac aac gac atc gtt acg gac tac agc      432
Lys Lys Lys Asp Val Lys Leu Tyr Asn Asp Ile Val Thr Asp Tyr Ser
            105                 110                 115

gag gag acg ctt gac tac tac gac aac cgc gta gcg tta gac acg gtt      480
Glu Glu Thr Leu Asp Tyr Tyr Asp Asn Arg Val Ala Leu Asp Thr Val
        120                 125                 130

aac caa ctt ctt gac gag gtt ctt gac ctt ttc tac cag cct aag ttc      528
Asn Gln Leu Leu Asp Glu Val Leu Asp Leu Phe Tyr Gln Pro Lys Phe
    135                 140                 145

gag ggc aag cag cgc atc gta ctt ggt ggc gac gag gtt tca ggc agc      576
Glu Gly Lys Gln Arg Ile Val Leu Gly Gly Asp Glu Val Ser Gly Ser
150                 155                 160                 165

gag gtt cac caa ctt gac ttc atc gac ttc atg aac cag atc gcg tct      624
Glu Val His Gln Leu Asp Phe Ile Asp Phe Met Asn Gln Ile Ala Ser
                170                 175                 180

acg gtt aag gag agc aag tac gag cca caa atg tgg aac gac agc atc      672
Thr Val Lys Glu Ser Lys Tyr Glu Pro Gln Met Trp Asn Asp Ser Ile
            185                 190                 195

acg tct gag ggc atc gcg aac ctt gac gac tct ttc tct atc ctt tac      720
Thr Ser Glu Gly Ile Ala Asn Leu Asp Asp Ser Phe Ser Ile Leu Tyr
        200                 205                 210

tgg cag cag tct acg ctt tct tct ggc gag gag tca ctt aac gtt gag      768
Trp Gln Gln Ser Thr Leu Ser Ser Gly Glu Glu Ser Leu Asn Val Glu
    215                 220                 225

gac ttc gag aac tgg ggc ttc tct gtt tac aac tac aat gcg tac agc      816
```

```
Asp Phe Glu Asn Trp Gly Phe Ser Val Tyr Asn Tyr Asn Ala Tyr Ser
230                 235                 240                 245

ctt tac ttc ctt cct tct aac ggc ttc acg cag gag gac atc aac gag      864
Leu Tyr Phe Leu Pro Ser Asn Gly Phe Thr Gln Glu Asp Ile Asn Glu
                250                 255                 260

cag atg gac tac atg aac tgg gcg tac gcg cac aac aag ttc ttc tac      912
Gln Met Asp Tyr Met Asn Trp Ala Tyr Ala His Asn Lys Phe Phe Tyr
            265                 270                 275

atc tct gac tac tac cac gcg gta gag acg tca aac gtt aag ggc agc      960
Ile Ser Asp Tyr Tyr His Ala Val Glu Thr Ser Asn Val Lys Gly Ser
        280                 285                 290

tca ctt acg ttc tgg ggt gag cac gcg acg gac ctt tca cag aag aaa     1008
Ser Leu Thr Phe Trp Gly Glu His Ala Thr Asp Leu Ser Gln Lys Lys
    295                 300                 305

ctt ctt aag cag gag ctt cct ctt atc cgc cac tac ctt aac ctt taa     1056
Leu Leu Lys Gln Glu Leu Pro Leu Ile Arg His Tyr Leu Asn Leu
310                 315                 320


<210> SEQ ID NO 8
<211> LENGTH: 351
<212> TYPE: PRT
<213> ORGANISM: Artificial Sequence
<220> FEATURE:
<223> OTHER INFORMATION: Synthetic Construct

<400> SEQUENCE: 8

Met Lys Lys Pro Leu Gly Lys Ile Val Ala Ser Thr Ala Leu Leu Ile
        -25                 -20                 -15

Ser Val Ala Phe Ser Ser Ser Ile Ala Ser Ala Gln Asp Gln Glu Lys
    -10                 -5                  -1  1               5

Gly Ile Thr Ile Asp Ile Ser Arg Lys His Tyr Thr Val Glu Thr Leu
                10                  15                  20

Lys Ser Leu Val Asp Glu Ile Ser Tyr Asn Gly Gly Asn Tyr Val Gln
            25                  30                  35

Leu His Phe Ser Asp Asn Glu Asn Tyr Ala Ile Ala Ser Glu Tyr Leu
        40                  45                  50

Gly Gln Ser Ser Glu Asn Thr Asn Asn Thr Tyr Leu Thr Lys Asn Glu
    55                  60                  65

Leu Leu Ser Leu Ile Ala Tyr Ser Asn Asp Lys Asp Ile Leu Val Ile
70                  75                  80                  85

Pro Asp Ile Asp Leu Pro Ala His Ser Lys Gly Trp Leu Glu Leu Ile
                90                  95                  100

Lys Lys Lys Asp Val Lys Leu Tyr Asn Asp Ile Val Thr Asp Tyr Ser
            105                 110                 115

Glu Glu Thr Leu Asp Tyr Tyr Asp Asn Arg Val Ala Leu Asp Thr Val
        120                 125                 130

Asn Gln Leu Leu Asp Glu Val Leu Asp Leu Phe Tyr Gln Pro Lys Phe
    135                 140                 145

Glu Gly Lys Gln Arg Ile Val Leu Gly Gly Asp Glu Val Ser Gly Ser
150                 155                 160                 165

Glu Val His Gln Leu Asp Phe Ile Asp Phe Met Asn Gln Ile Ala Ser
                170                 175                 180

Thr Val Lys Glu Ser Lys Tyr Glu Pro Gln Met Trp Asn Asp Ser Ile
            185                 190                 195

Thr Ser Glu Gly Ile Ala Asn Leu Asp Asp Ser Phe Ser Ile Leu Tyr
        200                 205                 210

Trp Gln Gln Ser Thr Leu Ser Ser Gly Glu Glu Ser Leu Asn Val Glu
```

```
    215                 220                 225

Asp Phe Glu Asn Trp Gly Phe Ser Val Tyr Asn Tyr Asn Ala Tyr Ser
230                 235                 240                 245

Leu Tyr Phe Leu Pro Ser Asn Gly Phe Thr Gln Glu Asp Ile Asn Glu
                250                 255                 260

Gln Met Asp Tyr Met Asn Trp Ala Tyr Ala His Asn Lys Phe Phe Tyr
            265                 270                 275

Ile Ser Asp Tyr Tyr His Ala Val Glu Thr Ser Asn Val Lys Gly Ser
        280                 285                 290

Ser Leu Thr Phe Trp Gly Glu His Ala Thr Asp Leu Ser Gln Lys Lys
    295                 300                 305

Leu Leu Lys Gln Glu Leu Pro Leu Ile Arg His Tyr Leu Asn Leu
310                 315                 320


<210> SEQ ID NO 9
<211> LENGTH: 1062
<212> TYPE: DNA
<213> ORGANISM: Artificial Sequence
<220> FEATURE:
<223> OTHER INFORMATION: SPamyLDisp45syn coding sequence
<220> FEATURE:
<221> NAME/KEY: CDS
<222> LOCATION: (1)..(1059)
<220> FEATURE:
<221> NAME/KEY: sig_peptide
<222> LOCATION: (1)..(84)
<220> FEATURE:
<221> NAME/KEY: mat_peptide
<222> LOCATION: (85)..(1059)

<400> SEQUENCE: 9

atg aaa caa caa aaa cgg ctt tac gcc cga ttg ctg acg ctg tta ttt       48
Met Lys Gln Gln Lys Arg Leu Tyr Ala Arg Leu Leu Thr Leu Leu Phe
            -25                 -20                 -15

gcg ctc atc ttc ttg ctg cct cat tct gca gca gcg gcg cag gac cag       96
Ala Leu Ile Phe Leu Leu Pro His Ser Ala Ala Ala Ala Gln Asp Gln
        -10                 -5              -1  1

gag aag ggc atc acg atc gac atc tca cgc aag cac tac acg gtt gag      144
Glu Lys Gly Ile Thr Ile Asp Ile Ser Arg Lys His Tyr Thr Val Glu
5                   10                  15                  20

acg ctt aag tca ctt gtt gac gag atc tca tac aat ggt ggc aac tac      192
Thr Leu Lys Ser Leu Val Asp Glu Ile Ser Tyr Asn Gly Gly Asn Tyr
                25                  30                  35

gtt cag ctt cac ttc tct gac aac gag aac tac gcg atc gcg tca gag      240
Val Gln Leu His Phe Ser Asp Asn Glu Asn Tyr Ala Ile Ala Ser Glu
            40                  45                  50

tac ctt ggc caa tca tct gag aac acg aac aac acg tac ctt acg aag      288
Tyr Leu Gly Gln Ser Ser Glu Asn Thr Asn Asn Thr Tyr Leu Thr Lys
        55                  60                  65

aac gag ctt ctt tca ctt atc gcg tac tct aac gac aag gac atc ctt      336
Asn Glu Leu Leu Ser Leu Ile Ala Tyr Ser Asn Asp Lys Asp Ile Leu
    70                  75                  80

gtt atc cct gac atc gac ctt cct gcg cac tct aag ggc tgg ctt gag      384
Val Ile Pro Asp Ile Asp Leu Pro Ala His Ser Lys Gly Trp Leu Glu
85                  90                  95                  100

ctt atc aag aag aag gac gtt aaa ctt tac aac gac atc gtt acg gac      432
Leu Ile Lys Lys Lys Asp Val Lys Leu Tyr Asn Asp Ile Val Thr Asp
                105                 110                 115

tac agc gag gag acg ctt gac tac tac gac aac cgc gta gcg tta gac      480
Tyr Ser Glu Glu Thr Leu Asp Tyr Tyr Asp Asn Arg Val Ala Leu Asp
            120                 125                 130
```

```
acg gtt aac caa ctt ctt gac gag gtt ctt gac ctt ttc tac cag cct      528
Thr Val Asn Gln Leu Leu Asp Glu Val Leu Asp Leu Phe Tyr Gln Pro
        135                 140                 145

aag ttc gag ggc aag cag cgc atc gta ctt ggt ggc gac gag gtt tca      576
Lys Phe Glu Gly Lys Gln Arg Ile Val Leu Gly Gly Asp Glu Val Ser
    150                 155                 160

ggc agc gag gtt cac caa ctt gac ttc atc gac ttc atg aac cag atc      624
Gly Ser Glu Val His Gln Leu Asp Phe Ile Asp Phe Met Asn Gln Ile
165                 170                 175                 180

gcg tct acg gtt aag gag agc aag tac gag cca caa atg tgg aac gac      672
Ala Ser Thr Val Lys Glu Ser Lys Tyr Glu Pro Gln Met Trp Asn Asp
                185                 190                 195

agc atc acg tct gag ggc atc gcg aac ctt gac gac tct ttc tct atc      720
Ser Ile Thr Ser Glu Gly Ile Ala Asn Leu Asp Asp Ser Phe Ser Ile
            200                 205                 210

ctt tac tgg cag cag tct acg ctt tct tct ggc gag gag tca ctt aac      768
Leu Tyr Trp Gln Gln Ser Thr Leu Ser Ser Gly Glu Glu Ser Leu Asn
        215                 220                 225

gtt gag gac ttc gag aac tgg ggc ttc tct gtt tac aac tac aat gcg      816
Val Glu Asp Phe Glu Asn Trp Gly Phe Ser Val Tyr Asn Tyr Asn Ala
    230                 235                 240

tac agc ctt tac ttc ctt cct tct aac ggc ttc acg cag gag gac atc      864
Tyr Ser Leu Tyr Phe Leu Pro Ser Asn Gly Phe Thr Gln Glu Asp Ile
245                 250                 255                 260

aac gag cag atg gac tac atg aac tgg gcg tac gcg cac aac aag ttc      912
Asn Glu Gln Met Asp Tyr Met Asn Trp Ala Tyr Ala His Asn Lys Phe
                265                 270                 275

ttc tac atc tct gac tac tac cac gcg gta gag acg tca aac gtt aag      960
Phe Tyr Ile Ser Asp Tyr Tyr His Ala Val Glu Thr Ser Asn Val Lys
            280                 285                 290

ggc agc tca ctt acg ttc tgg ggt gag cac gcg acg gac ctt tca cag     1008
Gly Ser Ser Leu Thr Phe Trp Gly Glu His Ala Thr Asp Leu Ser Gln
        295                 300                 305

aag aaa ctt ctt aag cag gag ctt cct ctt atc cgc cac tac ctt aac     1056
Lys Lys Leu Leu Lys Gln Glu Leu Pro Leu Ile Arg His Tyr Leu Asn
    310                 315                 320

ctt taa                                                             1062
Leu
325


<210> SEQ ID NO 10
<211> LENGTH: 353
<212> TYPE: PRT
<213> ORGANISM: Artificial Sequence
<220> FEATURE:
<223> OTHER INFORMATION: Synthetic Construct

<400> SEQUENCE: 10

Met Lys Gln Gln Lys Arg Leu Tyr Ala Arg Leu Leu Thr Leu Leu Phe
            -25                 -20                 -15

Ala Leu Ile Phe Leu Leu Pro His Ser Ala Ala Ala Ala Gln Asp Gln
        -10                 -5                  -1  1

Glu Lys Gly Ile Thr Ile Asp Ile Ser Arg Lys His Tyr Thr Val Glu
5                   10                  15                  20

Thr Leu Lys Ser Leu Val Asp Glu Ile Ser Tyr Asn Gly Gly Asn Tyr
                25                  30                  35

Val Gln Leu His Phe Ser Asp Asn Glu Asn Tyr Ala Ile Ala Ser Glu
            40                  45                  50

Tyr Leu Gly Gln Ser Ser Glu Asn Thr Asn Asn Thr Tyr Leu Thr Lys
        55                  60                  65
```

```
Asn Glu Leu Leu Ser Leu Ile Ala Tyr Ser Asn Asp Lys Asp Ile Leu
    70                  75                  80

Val Ile Pro Asp Ile Asp Leu Pro Ala His Ser Lys Gly Trp Leu Glu
85                  90                  95                  100

Leu Ile Lys Lys Lys Asp Val Lys Leu Tyr Asn Asp Ile Val Thr Asp
                105                 110                 115

Tyr Ser Glu Glu Thr Leu Asp Tyr Tyr Asp Asn Arg Val Ala Leu Asp
            120                 125                 130

Thr Val Asn Gln Leu Leu Asp Glu Val Leu Asp Leu Phe Tyr Gln Pro
        135                 140                 145

Lys Phe Glu Gly Lys Gln Arg Ile Val Leu Gly Gly Asp Glu Val Ser
    150                 155                 160

Gly Ser Glu Val His Gln Leu Asp Phe Ile Asp Phe Met Asn Gln Ile
165                 170                 175                 180

Ala Ser Thr Val Lys Glu Ser Lys Tyr Glu Pro Gln Met Trp Asn Asp
                185                 190                 195

Ser Ile Thr Ser Glu Gly Ile Ala Asn Leu Asp Asp Ser Phe Ser Ile
            200                 205                 210

Leu Tyr Trp Gln Gln Ser Thr Leu Ser Ser Gly Glu Glu Ser Leu Asn
        215                 220                 225

Val Glu Asp Phe Glu Asn Trp Gly Phe Ser Val Tyr Asn Tyr Asn Ala
    230                 235                 240

Tyr Ser Leu Tyr Phe Leu Pro Ser Asn Gly Phe Thr Gln Glu Asp Ile
245                 250                 255                 260

Asn Glu Gln Met Asp Tyr Met Asn Trp Ala Tyr Ala His Asn Lys Phe
                265                 270                 275

Phe Tyr Ile Ser Asp Tyr Tyr His Ala Val Glu Thr Ser Asn Val Lys
            280                 285                 290

Gly Ser Ser Leu Thr Phe Trp Gly Glu His Ala Thr Asp Leu Ser Gln
        295                 300                 305

Lys Lys Leu Leu Lys Gln Glu Leu Pro Leu Ile Arg His Tyr Leu Asn
    310                 315                 320

Leu
325
```

<210> SEQ ID NO 11
<211> LENGTH: 8
<212> TYPE: PRT
<213> ORGANISM: Artificial Sequence
<220> FEATURE:
<223> OTHER INFORMATION: motif
<220> FEATURE:
<221> NAME/KEY: MISC_FEATURE
<222> LOCATION: (1)..(1)
<223> OTHER INFORMATION: Xaa = V (Val) or I (Ile) or M (Met)
<220> FEATURE:
<221> NAME/KEY: MISC_FEATURE
<222> LOCATION: (2)..(2)
<223> OTHER INFORMATION: Xaa = L (Leu) or I (Ile) or V (Val)
<220> FEATURE:
<221> NAME/KEY: MISC_FEATURE
<222> LOCATION: (4)..(4)
<223> OTHER INFORMATION: Xaa = G (Gly) or A (Ala) or V (Val)
<220> FEATURE:
<221> NAME/KEY: MISC_FEATURE
<222> LOCATION: (7)..(7)
<223> OTHER INFORMATION: Xaa = V (Val) or I (Ile)
<220> FEATURE:
<221> NAME/KEY: MISC_FEATURE
<222> LOCATION: (8)..(8)
<223> OTHER INFORMATION: Xaa = P (Pro) or S (Ser) or A (Ala)

```
<400> SEQUENCE: 11

Xaa Xaa Gly Xaa Asp Glu Xaa Xaa
1               5
```